United States Patent [19]

Benoit et al.

[11] Patent Number: 5,530,156
[45] Date of Patent: Jun. 25, 1996

[54] PREPARATION OF O-IMINOOXYMETHYLBENZOIC ACID

[75] Inventors: Remy Benoit, Ludwigshafen; Hubert Sauter, Mannheim, both of Germany

[73] Assignee: BASF Aktiengesellschaft, Ludwigshafen, Germany

[21] Appl. No.: 314,908

[22] Filed: Sep. 29, 1994

Related U.S. Application Data

[62] Division of Ser. No. 41,848, Apr. 2, 1993, Pat. No. 5,393,920.

[30] Foreign Application Priority Data

Apr. 4, 1992 [DE] Germany .......................... 42 11 350.4

[51] Int. Cl.⁶ ........................................... C07C 249/00
[52] U.S. Cl. ........................................... 562/440
[58] Field of Search .................................. 562/440

[56] References Cited

FOREIGN PATENT DOCUMENTS

| | | |
|---|---|---|
| 0272487 | 6/1988 | European Pat. Off. . |
| 0370629 | 5/1990 | European Pat. Off. . |
| 0472300A2 | 7/1991 | European Pat. Off. ............... 562/400 |
| 0463488 | 1/1992 | European Pat. Off. . |
| 0472300 | 2/1992 | European Pat. Off. . |

OTHER PUBLICATIONS

Chemical Abstracts, issued 1969, Pifferie et al, "2,4-benzoxazines with potential central nervous system activity", Pifferi et al, 72:78959 1969, Ann. Chim. (Rome), 59(12), pp. 1136–1151.

Primary Examiner—Marianne M. Cintins
Assistant Examiner—Keith MacMillan
Attorney, Agent, or Firm—Oblon, Spivak, McClelland, Maier & Neustadt

[57] ABSTRACT o-Iminooxymethylbenozic acids of the general formula I

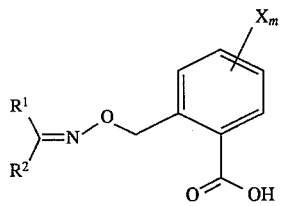

are disclosed
where, m, X, $R^1$ and $R^2$ are defined herein.

3 Claims, No Drawings

PREPARATION OF O-IMINOOXYMETHYLBENZOIC ACID

This is a Division of application Ser. No. 08/041,848 filed on Apr. 2, 1993, U.S. Pat. No. 5,393,920.

The present invention relates to a novel process for preparing an o-iminooxymethylbenzoic acid of the general formula I

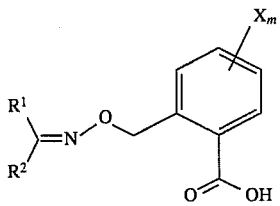

where m is an integer from 0 to 3,

X is unbranched or branched $C_1$–$C_4$-alkyl; unbranched or branched $C_1$–$C_4$-alkoxy, nitro, cyano or halogen, $R^1$ and $R^2$ are identical or different and each is hydrogen, cyano, hydroxyl, unbranched or branched $C_1$–$C_{10}$-alkyl, $C_1$–$C_4$-haloalkyl, $C_3$–$C_6$-cycloalkyl, $C_3$–$C_6$-halocycloalkyl, $C_3$–$C_6$-cycloalkyl-$C_1$–$C_4$-alkyl, $C_1$–$C_4$-alkoxy-$C_1$–$C_4$-alkyl, $C_1$–$C_4$-alkylthio-$C_1$–$C_4$-alkyl, arylthio-$C_1$–$C_4$-alkyl, $C_2$–$C_6$-alkenyl, $C_2$–$C_5$-haloalkenyl, $C_3$–$C_6$-cycloalkenyl, $C_3$–$C_6$-halocycloalkenyl, $C_2$–$C_5$-alkynyl, $C_1$–$C_6$-alkoxy, $C_1$–$C_6$-haloalkoxy, $C_1$–$C_4$-alkylthio, benzylthio, benzylamino, $C_1$–$C_4$-alkylcarbonyl, unsubstituted or substituted phenylcarbonyl, unsubstituted or substituted benzylcarbonyl, $C_1$–$C_4$-alkoxycarbonyl, unsubstituted or substituted phenoxycarbonyl, unsubstituted or substituted benzyloxycarbonyl, unsubstituted or substituted aryl, unsubstituted or substituted aryloxy, unsubstituted or substituted arylthio, unsubstituted or substituted aryl-$C_1$–$C_4$-alkyl, unsubstituted or substituted aryl-$C_2$–$C_4$-alkenyl, unsubstituted or substituted aryloxy-$C_1$–$C_4$-alkyl, unsubstituted or substituted arylthio-$C_1$–$C_4$-alkyl, unsubstituted or substituted hetaryl, unsubstituted or substituted hetaryloxy, unsubstituted or substituted hetarylthio, unsubstituted or substituted heteroaryl-$C_1$–$C_4$-alkyl, unsubstituted or substituted hetaryl-$C_2$–$C_4$-alkenyl, unsubstituted or substituted hetaryloxy-$C_1$–$C_4$-alkyl, hetarylthio-$C_1$–$C_4$-alkyl, unsubstituted or substituted heterocyclyl, or unsubstituted or substituted heterocyclyloxy or $N(R^6)_2$ where the meanings of the two $R^6$ radicals are identical or different and are H, $C_1$–$C_6$-alkyl, or unsubstituted or substituted phenyl, or —CO—$N(R^7)_2$, where the meanings of the two $R^7$ radicals are identical or different and are H, $C_1$–$C_4$-alkyl or unsubstituted or substituted phenyl, where unsubstituted or substituted includes, in addition to hydrogen, the radicals halogen, cyano, nitro, $C_1$–$C_4$-alkyl, $C_1$–$C_4$-alkoxy, $C_1$–$C_4$-haloalkyl, $C_1$–$C_4$-haloalkoxy, $C_1$–$C_{10}$-alkoximino-$C_1$–$C_2$-alkyl, aryl, aryloxy, benzyloxy, hetaryl, hetaryloxy, $C_3$–$C_6$-cycloalkyl, heterocyclyl or heterocyclyloxy, or $R^1$ and $R^2$, together with the C atom whose substituents they are, form a carbocyclic or heterocyclic ring which can be substituted by the radicals mentioned above under unsubstituted or substituted or $R^1$ or $R^2$ is halogen or the group

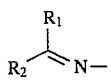

is the radical

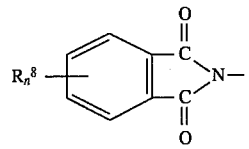

where n is the integers from 1 to 4, the radicals $R^8$ are identical or different and each is H, halogen, cyano, nitro, unsubstituted or substituted $C_1$–$C_4$-alkyl, $C_1$–$C_4$-alkoxy, $C_1$–$C_4$-haloalkyl, $C_1$–$C_4$-haloalkoxy, aryl, aryloxy, benzyloxy, hetaryl or hetaryloxy, by reacting an oxime of the general formula II

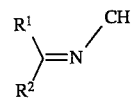

where $R^1$ and $R^2$ have the abovementioned meanings, with a lactone of the general formula III

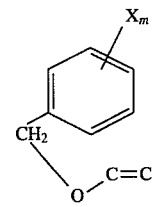

where X and m have the abovementioned meanings, if appropriate in the presence of a base or of a diluent or of a mixture thereof.

o-Iminooxymethylbenzoic acids are described in EP 234,045 (p. 97). The synthesis there starts from benzyl bromide i, which can be prepared in turn from methyl o-methylbenzoate by bromination according to methods known per se (see Organikum, p. 212) and which is then reacted with the salt of an oxime (EP 234,045, p. 97). In the last step, the ester group is hydrolyzed in the customary manner to liberate the acid.

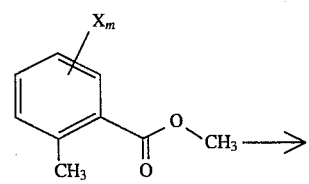

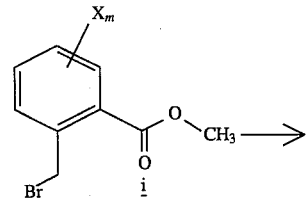

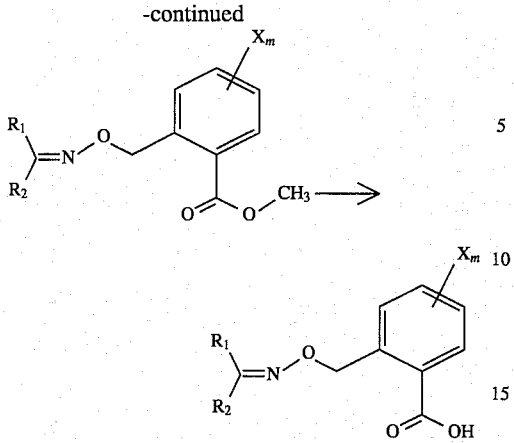

The preparation and reaction of the benzyl bromide i are particularly a problem. In particular on the large scale, working with bromine or N-bromosuccinimide is complicated and troublesome. Bromine-containing waste products furthermore have to be disposed of.

This method of preparation has the crucial disadvantage of being a long and multi-step process. The yields, in particular the space-time yield, are poor. As a result of this, the preparation of the intermediates of the formula I by the known process is very troublesome, undesired waste products being produced.

It is an object of the present invention to prepare the compounds I in an industrially more practicable way.

We have found that this object is achieved by the process described above.

The invention further relates to a process for preparing an o-iminooxymethylbenzoic acid I, wherein a) an oxime of the general formula II

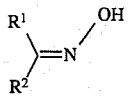  II is converted into the corresponding salt by means of a base in the presence of a diluent, b) this salt is mixed with a lactone of the general formula III

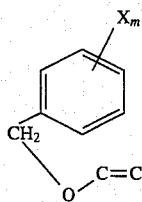  III and c) the mixture is further reacted in solution at from 20° to 250° C., or d) the diluent is distilled off and the mixture is reacted in the molten state at from 50° to 250° C.

Useful bases are in particular alkali metal hydroxides such as sodium hydroxide and potassium hydroxide and alkali metal alkoxides and alkaline earth metal alkoxides such as sodium methoxide, sodium ethoxide and potassium methoxide and metal hydrides such as sodium hydride; the alkali metal alkoxides and the metal hydrides are particularly preferred.

As a rule, process step (a) is carried out in the presence of a solvent or diluent, the reaction temperature normally being from 0° to 100° C., preferably from 20° to 80° C.

Suitable solvents or diluents are aromatic hydrocarbons such as benzene, toluene and o-, m- or p-xylene, alcohols such as methanol, ethanol and isopropanol, ethers such as dimethoxyethane or tetrahydrofuran, or liquids such as acetonitrile, dimethylformamide, N-methylpyrrolidone, dimethylpropyleneurea or mixtures of said solvents. Methanol and ethanol, dimethylformamide and N-methylpyrrolidone are particularly preferred.

The amount of base is not critical. For complete conversion of the oxime II to the corresponding salt (oximate) at least equimolar amounts of base are required; preferably an excess of 1 to 6 mol % of base are used, based on the amount of lactone III.

The salts of the oxime (oximate) II are advantageously mixed with the lactones of the formula III without isolation from the reaction mixture and fused together with simultaneous removal of the solvent or further reacted in the diluent.

In general, process step (d) is carried out at from 50° to 250° C., preferably from 160° to 200° C. In this process, with a decreasing amount of diluent the lactone III is converted from the dissolved to the liquid state and a readily miscible solution of the oximate in the lactone III is obtained.

Process step (c) is carried out at from 50° to 200° C., preferably from 60° to 160° C.

Normally, the oximate and lactone are employed in an approximately stoichiometric ratio, but in some cases an excess of one or the other component, for example up to 10 mol %, may be advisable.

In process steps (a) to (d), no particular conditions with respect to the pressure are necessary; the process is therefore expediently carried out at atmospheric pressure.

After the reaction has ended, the reaction mixture or the melt is diluted with water. The solution obtained is acidified, preferably with an inorganic acid such as hydrochloric acid or sulfuric acid, to liberate the o-iminooxymethylbenzoic acid I. Further working-up is carried out in the customary manner.

The compounds of the formula I prepared by the process according to the invention can basically be obtained as E/Z mixtures with respect to the C=N double bond if $R^1$ and $R^2$ are different. As a rule, however, far more predominantly, if not exclusively, only one isomer is obtained if $R^1$ and $R^2$ are sterically sufficiently different.

The process according to the invention can be carried out either batchwise or continuously. In the continuous procedure, the reactants are passed, for example, through a tubular reactor or over stirring vessel cascades.

The preparation method described can be used successfully for the synthesis of the o-iminooxymethylbenzoic acids of the formula I defined, in particular for those compounds in which the substituents $R^1, R^2$, X and m have the following meanings:

m is an integer from 0 to 2 (in particular 0 or 1).

X is methyl, ethyl, isopropyl, methoxy, nitro, cyano, fluorine, chlorine or bromine.

$R^1$ is hydrogen; cyano; $C_1$–$C_6$-alkyl (in particular methyl, ethyl, n-propyl, isopropyl or butyl); $C_3$–$C_6$-cycloalkyl (in particular cyclopropyl); $C_1$–$C_4$-alkylthio (in particular methylthio, ethylthio, n-propylthio or isopropylthio); $C_1$–$C_4$-alkyl thioalkyl (in particular methylthiomethylene); arylthioalkyl (in particular phenylthiomethylene); $C_1$–$C_4$-alkoxy(in particular methoxy, ethoxy, n-propoxy or isopropoxy); $C_1$–$C_4$-alkoxyalkyl (in particular methoxymethylene or ethoxymethylene); aryloxyalkyl (in particular phenoxymethylene); $C_1$–$C_4$-alkylamino (in particular methylamino, ethylamino, n-propylamino or isopropylamino); $C_1$–$C_3$-dialkylamino (in particular dimethylamino or diethylamino); benzylamino; benzylthio; benzyloxy; benzyl; vinyl; E-chlorovinyl; E-bromovinyl; —OH; $NH_2$; —CO—$NHCH_3$; —CONHEt; —CONHnPr; —CONHiPr; —CON($CH_3$)$_2$; —CON(Et)$_2$; —COOCH$_3$; —COOEt; —COOnPr; or —COOiPr.

$R^2$ is $C_1$–$C_4$-alkyl (in particular methyl, ethyl, n-propyl, i-propyl or n-butyl); phenyl [unsubstituted or substituted by 0 to 3 groups selected from $C_1$–$C_4$-alkoxy (in particular methoxy, ethoxy or i-propoxy); $C_1$–$C_4$-alkylthio (in particular methylthio or ethylthio); fluorine; chlorine; bromine; iodine; $C_1$–$C_4$-alkyl (in particular methyl, ethyl, n-propyl, isopropyl, n-butyl or tert-butyl); $C_3$–$C_6$-cycloalkyl (in particular cyclopropyl, cyclopentyl or cyclohexyl); nitro; cyano; trifluoromethyl; trichloromethyl; phenyl; phenoxy; benzyl; benzyloxy; hetaryl (in particular pyridinyl, pyrimidinyl, pyrazinyl, pyridazinyl, thienyl, furyl, pyrrolyl, pyrazolyl, imidazolyl, thiazolyl, isothiazolyl, oxazolyl or isoxazolyl); heterocyclyl (in particular morpholinyl, pyrrolidinyl, thiomorpholinyl, piperidinyl, piperazinyl, tetrahydrofuryl, tetrahydrothienyl, tetrahydropyranyl or tetrahydrothiopyranyl); hetaryloxy (in particular pyridinyloxy, pyrimidinyloxy, pyrazinyloxy or pyridazinyloxy); $C_1$–$C_4$-alkylcarbonyl (in particular —COMe, —COEt, —COnPr, —COiPr, —COnBu or —CO tert-Bu); $C_1$–$C_4$-alkoxycarbonyl (in particular —COOMe, —COOEt, —COOnPr, —COOiPr, —COOnBu or —COO tert-Bu); $C_1$–$C_4$-alkylaminocarbonyl (in particular —CONHMe, —CONHEt, —CONHPr, —CONHiPr, —CONHnBu, —CONH tert-Bu); $C_1$–$C_4$-dialkylaminocarbonyl (in particular —CON(Me)$_2$, -CON(Et)$_2$); or $C_1$–$C_4$-dialkylamino (in particular —N(Me)2, —N(Et)$_2$); Ph(Me)N—; Ph(Et)N—; —SO$_2$Me; —SO$_2$Et; —SOMe; —SOEt; —SO$_2$N(Me)$_2$; —SO$_2$N(Et)$_2$; —C(Me)=N—OMe; —C(Me)=N—OEt; —C(Me)=N—OnPr; —C(Me)=N—OiPr; —C(Me)=N—OnBu; —C(Me)=N—OtertBu; —C(Me)=N—Obenzyl; —C(Et)=N—OMe; —C(Et)=N—OEt; —C(Et)=N—OnPr; —C(Et)=N—OiPr; —C(Et)=N—OnBu; —C(Et)=N—OtertBu; —C(Et)=N—Obenzyl; —C(nPr)=N—OMe; —C(nPr)=N—OEt; —C(npr)=N—OnPr; —C(NPr)=N—OiPr; —C(nPr)=N—OnBu; —C(nPr)=N—OtertBu; —C(nPr)=N—Obenzyl; —C(iPr)=N—OMe; —C(iPr)=N—OEt; —C(iPr)=OnPr; —C(iPr)=N—OiPr; —C(iPr)=N—OnBu; —C(iPr)=N—OtertBu; —C(iPr)=N—Obenzyl];

naphthyl [unsubstituted or substituted by 0 to 3 groups selected from $C_1$–$C_4$-alkyl (in particular methyl, ethyl, n-propyl or isopropyl); $C_1$–$C_4$-alkoxy (in particular methoxy, ethoxy, n-propoxyor isopropoxy); $C_1$–$C_4$-alkylthio (in particular methylthio or ethylthio); or F, Cl, Br, $NO_2$ or CN];

hetaryl (in particular pyridinyl, pyrimidinyl, pyrazinyl, pyridazinyl, triazinyl, quinolyl, quinoxalyl, naphthyridinyl, trizolyl, imidazolyl, pyrazolyl, thiazolyl, isothiazolyl, oxazolyl, isoxazolyl, oxadiazolyl, thiadiazolyl, thienyl, furyl, pyrrolyl, benzothienyl, benzofuryl, indolyl, benzimidazolyl, benzopyrazolyl, benzothiazolyl, benzisothiazolyl, benzoxazolyl or benzisoxazolyl) where the hetaryl can be substituted by 0 to 2 substituents, selected from methyl, ethyl, i-propyl, n-propyl, n-butyl, tert-butyl, cyclopropyl, F, Cl, Br, I, methoxy, ethoxy, n-propoxy, i-propoxy, cyano, nitro, COOMe, COOEt, COOnPr, COOiPr, CONHMe, CONHEt, CON(Me)$_2$, CON(Et)$_2$, methylthio, ethylthio, —COCH$_3$, —COEt, —COiPr, —COnPr, phenyl and phenoxy;

phenylcarbonyl [where the phenyl ring can be substituted by 0 to 3 substituents, selected from: methyl, ethyl, n-propyl, i-propyl, n-butyl, tert-butyl, cyclopropyl, MeO, EtO, nPrO, iPrO, MeS, EtS, F, Cl, Br, I, $NO_2$, cyano or trifluoromethyl] or the radical

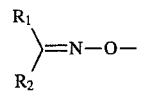

can have the following meanings

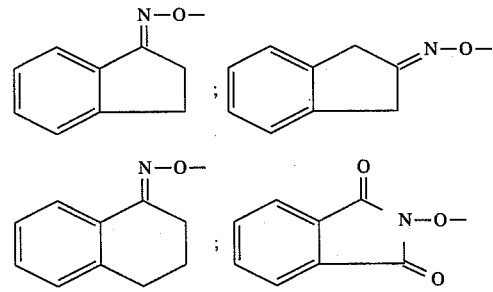

The o-iminooxymethylbenzoic acids of the formula I are surprisingly obtained in high yield and excellent purity by the process according to the invention. This was not to be expected from the prior art. In particular, it was in no case to be foreseen that the salt of the oxime (oximate) could be reacted readily in this reaction at high temperatures (100°–160° C.) without decomposing. Compared to the prior art, the process according to the invention has a number of advantages. It can be carried out in a very simple manner on the industrial scale. It does not require the use of bromine or possibly chlorine or N-bromosuccinimide or N-chlorosuccinimide. It thus avoids the formation of halogen-containing waste products and is therefore industrially simpler and fairly problem-free. Corrosion problems due to halogen are additionally avoided. A significant advantage of this process is furthermore that it leads to the acids of the formula I in a one-step, industrially simple and problem-free process.

A further advantage is that in one variant of the process the alkali metal oximate produced as an intermediate does not have to be isolated as a solid, but that a fluid transition from a solution or suspension of the oximate from the diluent to the melt (oximate+ lactone III) takes place. This is achieved by adding the lactone III to the salt of the oxime II in the presence of a diluent and then distilling off the diluent.

In another variant, the oximate can be further reacted with the phthalide in a solvent. The flexibility of the reaction procedure in the context indicated enables the optimum conditions to be selected for the particular individual case.

The o-iminooxymethylbenzoic acids I are useful intermediates for preparing o-iminooxymethylphenyl esters IX and X, which are used in plant protection, in particular as fungicides [cf. EP-A 370,629; EP-A 414,155; EP-A 426,460; EP-A 460,575; WO 70/07493).
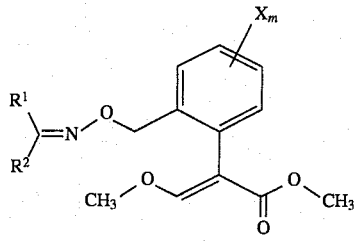
IX
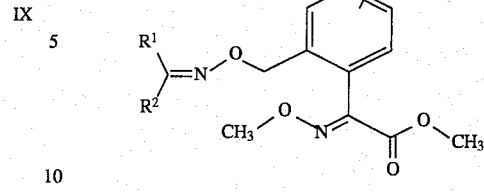
X
In the following reaction scheme, two particularly preferred synthetic routes for preparing the compounds IX from o-iminooxymethylbenzoic acid are shown:
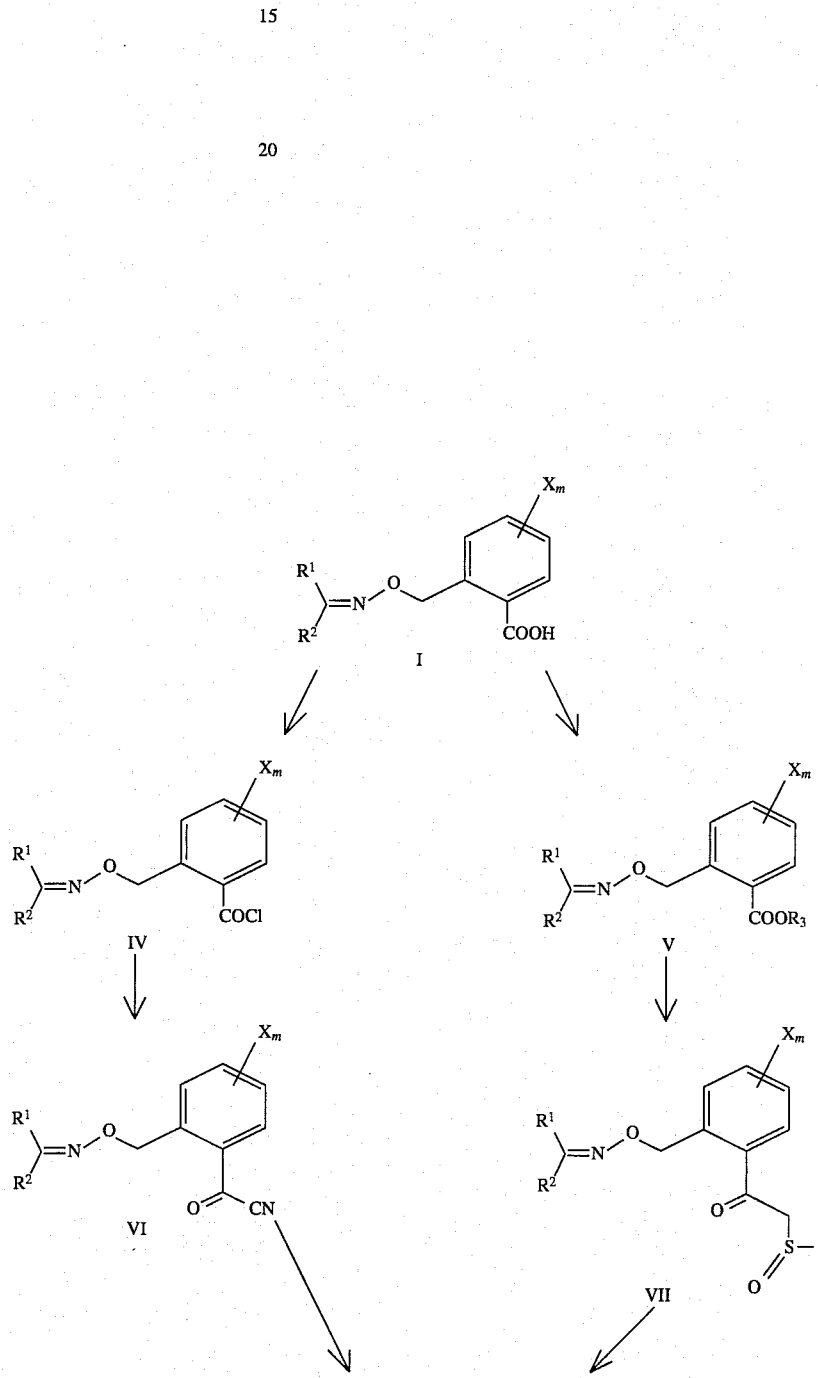

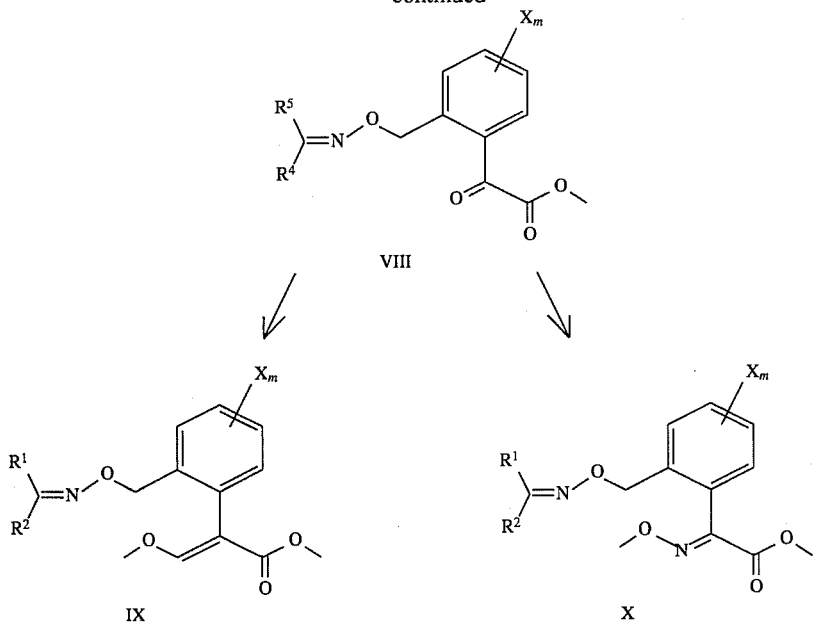

The benzoic acids I are advantageously converted into their acid chlorides by this process (cf. Organikum, VEB Deutscher Verlag der Wissenschaften, 16th edition, Berlin, 1986, page 423 et seq.) and the corresponding benzoyl cyanides VI are prepared from these, using an aqueous organic two-phase system and in the presence of a phase-transfer catalyst [Tetrahedron Letters (1974) 2275].

The benzoyl cyanides IV are then reacted with lower alcohols by the Pinner reaction [cf. Angew. Chemie 94 (1982) 1], phenylglyoxylic acid ester VIII resulting. The α-ketoesters VIII are then reacted either with o-methylhydroxylamine (or a salt thereof) to obtain the bisoxime ether of the type X, or reacted with a methoxymethylenation reagent such as methoxymethylenetriphenylphosphorane (cf. EP 0,044,448, Jul. 4, 1980) to prepare the acrylic esters IX. In a second known process, the acid I is first converted into its corresponding esters V (cf. Organikum page 499). These esters V are then converted to the β-ketosulfoxide VII in the presence of base and dimethyl sulfoxide (J. Am. Chem. Soc. 88 (1966) 5498). The α-ketoesters VIII are then obtained by the Pummerer reaction by bromination of the compound VII in the presence of a base and rearrangement in an acid (cf. J. Am. Chem. Soc. 88 (1966) 5498 and Synthesis (1982) 41).

For the intermediates I, IV, V, VI and VII, the radicals $R^1$, $R^2$, X and m preferably have the following meanings:

m is an integer from 0 to 2 (in particular 0 or 1)

X is methyl, ethyl, isopropyl, methoxy, nitro, cyano, fluorine, chlorine or bromine.

$R^1$ is hydrogen; cyano; $C_1$–$C_6$-alkyl (in particular methyl, ethyl, n-propyl, isopropyl or butyl); $C_3$–$C_6$-cycloalkyl (in particular cyclopropyl); $C_1$–$C_4$-alkylthio (in particular methylthio, ethylthio, n-propylthio or isopropylthio); $C_1$–$C_4$-alkylthioalkyl (in particular methylthiomethylene); arylthioalkyl (in particular phenylthiomethylene); $C_1$–$C_4$-alkoxy (in particular methoxy, ethoxy, n-propoxy or isopropoxy); $C_1$–$C_4$-alkoxyalkyl (in particular methoxymethylene or ethoxymethylene); aryloxyalkyl (in particular phenoxymethylene); $C_1$–$C_4$-alkylamino (in particular methylamino, ethylamino, n-propylamino or isopropylamino); $C_1$–$C_3$-dialkylamino (in particular dimethylamino or diethylamino); benzylamino; benzylthio; benzyloxy; benzyl; vinyl; E-chlorovinyl; E-bromovinyl; —OH; $NH_2$; —CO—$NHCH_3$; —CONHEt; —CONHnPr; —CONHiPr; —CON$(CH_3)_2$; —CON$(Et)_2$; —$COOCH_3$; —COOEt; —COOnPr; or —COOiPr.

$R^2$ is $C_1$–$C_4$-alkyl (in particular methyl, ethyl, n-propyl, i-propyl or n-butyl); phenyl [unsubstituted or substituted by 0 to 3 groups selected from $C_1$–$C_4$-alkoxy (in particular methoxy, ethoxy or i-propoxy); $C_1$–$C_4$-alkylthio (in particular methylthio or ethylthio); fluorine; chlorine; bromine; iodine; $C_1$–$C_4$-alkyl (in particular methyl, ethyl, n-propyl, isopropyl, n-butyl or tert-butyl); $C_3$–$C_6$-cycloalkyl (in particular cyclopropyl, cyclopentyl or cyclohexyl); nitro; cyano; trifluoromethyl; trichloromethyl; phenyl; phenoxy; benzyl; benzyloxy; hetaryl (in particular pyridinyl, pyrimidinyl, pyrazinyl, pyridazinyl, thienyl, furyl, pyrrolyl, pyrazolyl, imidazolyl, thiazolyl, isothiazolyl, oxazolyl or isoxazolyl); heterocyclyl (in particular morpholinyl, pyrrolidinyl, thiomorpholinyl, piperidinyl, piperazinyl, tetrahydrofuryl, tetrahydrothienyl, tetrahydropyranyl or tetrahydrothiopyranyl); hetaryloxy (in particular pyridinyloxy, pyrimidinyloxy, pyrazinyloxy or pyridazinyloxy); $C_1$–$C_4$-alkylcarbonyl (in particular —COMe, —COEt, —COnPr, —COiPr, —COnBu or —CO tert-Bu); $C_1$–$C_4$-alkoxycarbonyl (in particular —COOMe, —COOEt, —COOnPr, —COOiPr, —COOnBu or —COO tert-Bu); $C_1$–$C_4$-alkylaminocarbonyl (in particular —CONHMe, —CONHEt, —CONHPr, —CONHiPr, —CONHnBu, —CONH tert-Bu); $C_1$–$C_4$-dialkylaminocarbonyl (in particular —CON$(Me)_2$, —CON$(Et)_2$); or $C_1$–$C_4$-dialkylamino (in particular —N$(Me)_2$, —N$(ET)_2$); Ph(Me)N—; Ph(Et)N—; —$SO_2$Me; —$SO_2$Et; —SOMe; —SOEt; —$SO_2$N$(Me)_2$; —$SO_2$N$(Et)_2$; —C(Me)=N—OMe; —C(Me)=N—OEt           —C(Me)=N—OnPr; —C(Me)=N—OiPr;           —C(Me)=N—OnBu; —C(Me)=N—OtertBu;       —C(Me)=N—Obenzyl; —C(Et)=N—OMe;               —C(Et)=N—OEt; —C(Et)=N—OnPr;               —C(Et)=N—OiPr;

=C(Et)=N—OnBu; —C(Et)=N—OtertBu;
—C(Et)=N—Obenzyl; —C(nPr)=N—OMe;
—C(nPr)=N—OEt; —C(nPr)=N—OnPr;
—C(NPr)=N—OiPr —C(nPr)=N—OnBu;
—C(nPr)=N—OtertBu; —C(nPr)=N—Obenzyl;
—C(iPr)=N—OMe; —C(iPr)=N—OEt;
—C(iPr)=OnPr; —C(iPr)=N—OiPr; —C(iPr)=N—OnBu; —C(iPr)=N—OtertBu; —C(iPr)=N—Obenzyl];

naphthyl [unsubstituted or substituted by 0 to 3 groups selected from $C_1$–$C_4$-alkyl (in particular methyl, ethyl, n-propyl or isopropyl); $C_1$–$C_4$-alkoxy (in particular methoxy, ethoxy, n-propoxyor isopropoxy); $C_1$–$C_4$-alkylthio (in particular methylthio or ethylthio); or F, Cl, Br, $NO_2$ or CN];

hetaryl (in particular pyridinyl, pyrimidinyl, pyrazinyl, pyridazinyl, triazinyl, quinolyl, quinoxalyl, naphthyridinyl, trizolyl, imidazolyl, pyrazolyl, thiazolyl, isothiazolyl, oxazolyl, isoxazolyl, oxadiazolyl, thiadiazolyl, thienyl, furyl, pyrrolyl, benzothienyl, benzofuryl, indolyl, benzimidazolyl, benzopyrazolyl, benzothiazolyl, benzisothiazolyl, benzoxazolyl or benzisoxazolyl) where the heteroaromatic can be substituted by 0 to 2 substituents, selected from methyl, ethyl, i-propyl, n-propyl, n-butyl, tert-butyl, cyclopropyl, F, Cl, Br, I, methoxy, ethoxy, n-propoxy, i-propoxy, cyano, nitro, COOMe, COOEr, COOnPr, COOiPr, CONHMe, CONHEt, CON(Me)$_2$, CON(Et)$_2$, methylthio, ethylthio, —COCH$_3$, —COEt, —COiPr, —COnPr, phenyl and phenoxy; phenylcarbonyl [where the phenyl ring can be substituted by 0 to 3 substituents, selected from: methyl, ethyl, n-propyl, i-propyl, n-butyl, tert-butyl, cyclopropyl, MeO, EtO, nPrO, iPrO, MeS, EtS, F, Cl, Br, I, NO$_2$, cyano or trifluoromethyl] or the radical

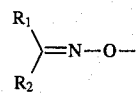

can have the following meanings

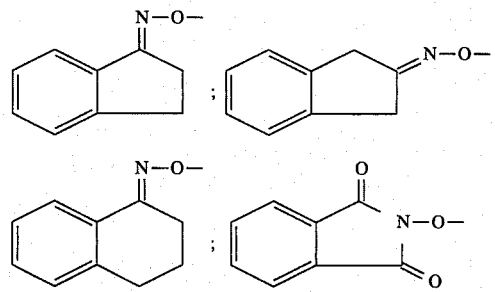

For the intermediate VIII, $R^4$ and $R^5$ preferably have the following meanings:

$R^4$ is benzyl; $C_1$–$C_4$-alkylcarbonyl (e.g. —COMe, —COEt, —COnPr, —COiPr, —COnBu, —COtertBu); $C_1$–$C_4$-alkoxycarbonyl (e.g. —COOMe, —COOEt, —COOnPr, —COOiPr, —COOnBu, —COOiBu, —COOtertBu); phenyl; naphthyl; pyridinyl; pyrimidinyl; pyrazinyl; pyridazinyl; triazinyl; quinolyl; quinoxalyl; naphthyridinyl; triazolyl; imidazolyl; pyrazolyl; thiazolyl; isothiazolyl; oxazolyl; isoxazolyl; oxadiazolyl; thiadiazolyl; thienyl; furyl; pyrrolyl; benzothienyl; benzofuryl; indolyl; benzimidazolyl; benzopyrazolyl; benzothiazolyl; benzisothiazolyl; benzoxazolyl; or benzisoxazolyl; it being possible for any aromatic or heteroaromatic ring to be substituted by 1 to 3 groups selected from: hydrogen; F; Cl; Br; I; nitro; cyano; $C_1$–$C_4$-alkyl (e.g. methyl, ethyl, n-propyl, i-propyl, n-butyl, i-butyl, tert-butyl); $C_1$–$C_4$-alkoxy (e.g. methoxy, ethoxy, n-propoxy, i-propoxy, n-butoxy, i-butoxy, tert-butoxy); trifluoromethyl; trichloromethyl; phenyl; phenoxy; or benzyloxy.

$R^5$ is hydrogen; $C_1$–$C_4$-alkyl (e.g. methyl, ethyl, n-propyl, i-propyl, n-butyl, i-butyl, tert-butyl); $C_1$–$C_4$-alkylcarbonyl (e.g. —COMe, —COEt, —COnPr, —COiPr, —COnBu, —COiBu, —COtert—Bu); $C_1$–$C_4$-alkoxycarbonyl (e.g. —COOMe, —COOEt, —COOnPr, —COOiPrn, —COOnBu, —COOiBu, —COO-tertBu); cyano; $C_1$–$C_4$-alkylthio ( e.g. —SMe, —SEt, —SnPr, —SiPr, —SnBu, —SiBu, —StertBu); $C_1$–$C_4$-alkoxy (e.g. —OMe, —OEt, —OnPr, OiPr, —OnBu, —OiBu, —OtertBu); $C_3$–$C_6$-cycloalkyl (e.g. cyclopropyl ); $NR^9R^{10}$.

$R^9$ is $C_1$–$C_4$-alkyl (e.g. methyl, ethyl, n-propyl, i-propyl ); phenyl $C_1$–$C_4$-alkyl (e.g. benzyl, 2-phenylethyl, 1-phenylethyl); or phenyl.

$R^{10}$ is hydrogen; $C_1$–$C_4$-alkyl (e.g. methyl, ethyl, n-propyl or i-propyl) or the radical

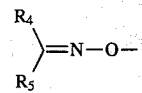

has the following meanings:

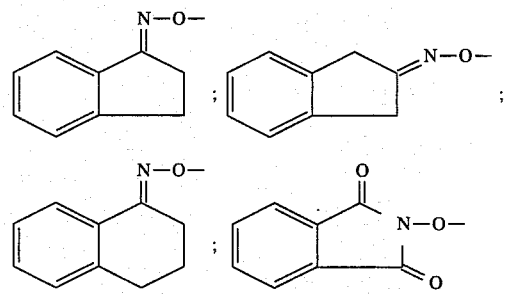

The Examples illustrate the invention.

EXAMPLE 1

Compound 32 in Table 1

25.4 g (0.15 mol) of p-chloroacetophenone oxime are dissolved in 150 ml of methanol using 27 g of a 30% strength (% by weight) sodium methoxide solution, the mixture is heated under reflux for 30 min, the methanol is distilled off, 20 g (0.15 mol) of phthalide are added and the mixture is heated at 180° C. for 2 hours. The heating is removed, 250 ml of water are cautiously added at 100° C., the mixture is extracted twice with methyl tert-butyl ether (MTBE) after cooling to 20° C., the aqueous phase is acidified to pH 2 with conc. $H_2SO_4$ and the precipitated solid is filtered off with suction. 25.9 g (57%) of crude acid are obtained. Warning: In the form of pure substances, the sodium salts of acetophenone oximes can decompose violently above 150° C. The following process variants (Examples 2 to 5) are therefore recommended for the reaction.

EXAMPLE 2

Compound 31 in Table 1

7.5 g (0.05 mol) of p-methylacetophenone oxime are dissolved in 30 ml of $CH_3OH$ under nitrogen gas using 9 g of a 30% strength sodium methoxide solution, the mixture is refluxed for 1 hour, 6.7 g (0.05 mol) of phthalide are added, the methanol is distilled off and the mixture is heated at 160° C. for 2 hours. After cooling to 20° C., 100 ml of water are added, the mixture is extracted twice with MTBE, and the aqueous phase is acidified to pH 2 with conc. $H_2SO_4$. The dark precipitated material is separated from the water and dissolved in MTBE, and the solution is dried and concentrated. 9.6 g (68 %) of crude acid are obtained.

EXAMPLE 3

Compound 31 in Table 1

2.6 g of NaH (55% strength) are introduced, 7.5 g (0.05 mol) of p-methylacetophenone oxime are dissolved in 50 ml of tetrahydrofuran (THF), added dropwise under nitrogen gas, and the mixture is heated at 60° C. for 1 hour, 50 ml of THF are added and it is cooled to 40° C. A solution of 6.7 g (0.05 mol) of phthalide in 30 ml of THF is added, the solvent is distilled off and the mixture is heated at 160° C. for 2 hours. After cooling, 100 ml of $H_2O$ are added, the mixture is extracted twice with MTBE, the aqueous phase is acidified to pH 2 with conc. $H_2SO_4$, the suspension is stirred with a little pentane, and the precipitate is filtered off with suction and washed with water. After drying in a vacuum drying oven 7.4 g (52 %) of crude acid are obtained.

EXAMPLE 4

Compound 31 in Table 1

2.6 g of NaH (55% strength) are introduced, 7.5 g (0.05 mol) of p-methylacetophenone oxime are added dropwise in 50 ml of dimethylformamide (DMF) under $N_2$, the mixture is stirred at 60° C. for a further hour, 50 ml of DMF are added dropwise and the suspension is refluxed for 2 hours. After cooling, 200 ml of $H_{20}$ are added, the mixture is acidified with conc. $H_2SO_4$, and the precipitate is filtered off with suction, washed with $H_2O$ and dried in a vacuum drying oven. 9.3 g (66%) of acid are obtained.

EXAMPLE 5

Compound 31 in Table 1

2.6 g of NaH (55% strength) are introduced, 7.5 g (0.05 mol) of p-methylacetophenone oxime are added dropwise in 50 ml of DMF under $N_2$, the mixture is stirred at 60° C. for a further hour and 50 ml of DMF are added, 6.7 g (0.05 mol) of phthalide in 50 ml of DMF are added dropwise, and the suspension is stirred at 100° C. for 6 hours and at 20° C. overnight. Water (200 ml) is then added, the mixture is acidified with conc. $H_2SO_4$, and the precipitate is filtered off with suction, washed with water and dried. 10.2 g (72%) of pale crystals of the acid are obtained. M.p.=152° C.

EXAMPLE 6

Compound 31 in Table 5

4 g (0.016 mol) of the acid (compound no. 31, Table 1) are dissolved in 20 ml of methanol, 2.5 g (0.028 mol) of $SOCl_2$ are added dropwise and the reaction mixture is refluxed for 1 hour. The solvent is evaporated on a rotary evaporator, the residue is dissolved in MTBE, the solution is washed with 10% strength $Na_2CO_3$ solution and dried with $Na_2SO_4$ and the solvent is evaporated. 3.4 g (82%) of oil are obtained.

EXAMPLE 7

Compound 32 in Table 5

12.5 g (0.041 mol) of the acid (compound 32 in Table 1) are dissolved in 50 ml of methanol, 7.4 g (0.083 mol) of $SOCl_2$ are added dropwise and the reaction mixture is refluxed for 2 hours. The solvent is evaporated on the rotary evaporator, the residue is dissolved in MTBE, the solution is washed three times with a 10% strength aqueous $Na_2CO_3$ solution and dried with $Na_2SO_4$ and the solvent is evaporated. 11.2 g (86%) of oil are obtained.

The following o-iminooxymethylbenzoic acids of the formula I can be prepared, for example, by the processes mentioned.

EXAMPLE 8

Compound 31 in Table 1

45.8 g of NaH (55% strength) are suspended in 1000 ml of DMF, 149 g (1 mol) of p-methylacetophenone oxime are added dropwise in 600 ml of DMF under $N_2$, the mixture is stirred at 60° C. for a further hour, 200 ml of DMF are added, 134 g (1 mol) of phthalide in 500 ml of DMF are added dropwise, and the suspension is stirred at 100° C. for 6 hours and at 20° C. overnight. Water (about 5 l) is then added, the mixture is acidified with conc. $H_2SO_4$, and the precipitate is filtered off with suction, washed with water and dried. 262 g (92%) of pale crystals of the acid are obtained. M.p.=152° C.

EXAMPLE 9

Compound 46 in Table 1

2.65 g of NaH (55% strength) are suspended in 50 ml of DMF, 7.05 g of 3-acetylthiophene oxime are added dropwise in 50 ml of DMF under $N_2$, the mixture is stirred at 60° C. for a further hour, 6.7 g of phthalide in 50 ml of DMF are added dropwise, and the suspension is stirred at 100° C. for 8 hours. After cooling, about 150 ml of $H_2O$ are added, the mixture is acidified with conc. $H_2SO_4$, and the precipitate is filtered off with suction, washed with water and dried. 9 g (65%) of crystals of the acid are obtained. M.p.=149°–151° C.

EXAMPLE 10

Compound 31 in Table 6

1.75 g of DMSO are initially introduced into 5 ml of THF at −40° C., 25 g of butyllithium solution (1.6M) are added dropwise at −40° C. under $N_2$, the mixture is further stirred at 0° C. until outgassing ceases, compound 31 Tab. 5 in 15 ml of THF is added dropwise at −40° C. and the mixture is stirred at RT for 2 hours. The reaction mixture is hydrolyzed using an $NH_4Cl$ solution, acidified with 2N HCl and extracted with MTBE, and the organic phase is neutralized using solid $Na_2CO_3$, dried and concentrated. After chromatographic separation, 2.9 g (42%) of compound 31 in Table 6 are obtained.

EXAMPLE 11

Compound 31 in Table 4

2.9 g of compound 31 in Table 6 are dissolved in 30 ml of acetone, 1.3 g of dibromodimethylhydantoin are added at RT, and the mixture is stirred at RT for a further 15 min and concentrated. The residue is dissolved in 40 ml of methanol, 2 ml of conc. HCl are added and stirring of the solution is continued at RT for 2 h. The reaction mixture is taken up in MTBE/water, and the organic phase is washed with $Na_2CO_3$ and water, dried and concentrated. The product is chromatographed and 0.6 g of a mixture of p-methylacetophenone and compound 31 in Table 4 is obtained.

$^1$H-NMR (CDCl$_3$/TMS): 2.25 (s,3H); 2.35(s,3H); 3.90(s, 3H); 5.55(s,2H); 7.05–7.80 (m,8H) ppm.

EXAMPLE 12

Compound 31 in Table 2

10 g of compound 31 in Table 1 are suspended in 80 ml of toluene, 8.3 g of pyridine and 2 drops of DMF are added, 6.25 g of SOCl$_2$ are added dropwise at 0° C., the cooling is removed and the mixture is stirred for a further 2 hours. The yellow precipitate is filtered off with suction and washed with toluene, and the mother liquor is concentrated. 5.3 g of crude product are obtained.

$^1$H-NMR (CDCl$_3$/TMS: 2.35 (s,6H); 5.70 (s,2H); 7.10–8.15 (m,8H) ppm.

EXAMPLE 13

Ethyl o-[1-(4-methylphenyl)ethyliminooxy-methyl]phenylgloxylate (Compound of type VIII where R$_4$=4-methylphenyl; R$_5$=methyl; R$_{11}$=ethyl)

3.0 g of compound 31 in Table 6 are dissolved in 30 ml of acetone, 1.4 g of dibromodimethylhydantoin are added at RT, and the mixture is stirred at RT for a further 15 min and concentrated. The residue is dissolved in 40 ml of ethanol, 2 ml of conc. HCl are added and stirring of the solution is continued at RT for 4 hours. The reaction mixture is taken up in MTBE/water, and the organic phase is neutralized using Na$_2$CO$_3$, dried and concentrated. The p-methylacetophenone formed is distilled in a bulb tube and the bottom is chromatographed. 0.4 g of ethyl o-[1-(4-methylphenyl)ethyliminooxymethyl]phenylglyoxylate is obtained.

$^1$H-NMR (CDCl$_3$/TMS): 1.35 (t,3H); 2.30 (s,3H); 2.35 (s,3H); 4.40 (q,2H); 5.55 (s,2H); 7.05–7.80 (m,8H) ppm.

IR: 1733; 1683; 1195; 1038; 1012 cm$^{-1}$.

The following o-iminooxymethylbenzoic acids of the formula I can be prepared, for example, by the processes mentioned.

TABLE 1

| No. | R$^1$ | R$^2$ | Data |
|---|---|---|---|
| 1 | —CN | -2-naphthyl | |
| 2 | —CN | -n-hexyl | |
| 3 | —CN | -cyclohexyl | |
| 4 | —CN | -thiophenyl | |
| 5 | —CN | -phenyl | |
| 6 | —CN | -4-Me-phenyl | |
| 7 | —CN | -4-chlorophenyl | |
| 8 | —CN | -4-tert-butyl | |
| 9 | —CN | -2-MeO-phenyl | |
| 10 | —CN | -4-i-Pr—O-phenyl | |
| 11 | —CN | -2-MeS-phenyl | |
| 12 | —CN | -2-fluorophenyl | |
| 13 | —CN | -3-trifluoromethylphenyl | |
| 14 | —CN | -3,5-dichlorophenyl | |
| 15 | —CN | -3-phenylphenyl | |
| 16 | —CN | -4-phenoxyphenyl | |
| 17 | —CN | -3-CH$_3$(C═N—OMe)-phenyl | |
| 18 | —CN | -3-CH$_3$(C═N—On—Bu)-phenyl | |
| 19 | —CN | -3-pyridyl | |
| 20 | —CN | -5-pyrimidinyl | |
| 21 | —CN | -3-thienyl | |
| 22 | —CN | -3-indolyl | |
| 23 | —CN | -5-(4-methylthiazolyl) | |
| 24 | —CN | -5-indazolyl | |
| 25 | —CN | -3-(6-chloropyridyl) | |
| 26 | —CN$_3$ | -2-naphthyl | |
| 27 | —CN$_3$ | -n-hexyl | |
| 28 | —CH$_3$ | -cyclohexyl | |
| 29 | —CH$_3$ | -thiophenyl | |
| 30 | —CH$_3$ | -phenyl | |
| 31 | —CH$_3$ | -4-Me-phenyl | IR: 1678; 1318; 1046; 820; 743 cm$^{-1}$ |
| 32 | —CH$_3$ | -4-chlorophenyl | IR: 1687; 1318; 1042; 945; 733 cm$^{-1}$ |
| 33 | —CH$_3$ | -4-tert-butyl | |

TABLE 1-continued

Structure I: 2-({[(R₁)(R₂)C=N]-O-CH₂})-benzoic acid

| No. | R¹ | R² | Data |
|---|---|---|---|
| 34 | —CH₃ | -2-MeO-phenyl | |
| 35 | —CH₃ | -4-i-Pr—O-phenyl | |
| 36 | —CH₃ | -2-MeS-phenyl | |
| 37 | —CH₃ | -2-fluorophenyl | |
| 38 | —CH₃ | -3-trifluoromethylphenyl | |
| 39 | —CH₃ | -3,5-dichlorophenyl | |
| 40 | —CH₃ | -3-phenylphenyl | |
| 41 | —CH₃ | -4-phenoxyphenyl | |
| 42 | —CH₃ | -3-CH₃(C=N—OMe)-phenyl | |
| 43 | —CH₃ | -3-CH₃(C=N—On—Bu)-phenyl | |
| 44 | —CH₃ | -3-pyridyl | |
| 45 | —CH₃ | -5-pyrimidinyl | |
| 46 | —CH₃ | -3-thienyl | IR: 1677; 1320; 1044; 780 738 cm⁻¹ |
| 47 | —CH₃ | -3-indolyl | |
| 48 | —CH₃ | -5-(4-methylthiazolyl) | |
| 49 | —CH₃ | -5-indazolyl | |
| 50 | —CH₃ | -3-(6-chloropyridyl) | |
| 51 | —OCH₃ | -2-naphthyl | |
| 52 | —OCH₃ | -n-hexyl | |
| 53 | —OCH₃ | -cyclohexyl | |
| 54 | —OCH₃ | -thiophenyl | |
| 55 | —OCH₃ | -phenyl | |
| 56 | —OCH₃ | -4-Me-phenyl | |
| 57 | —OCH₃ | -4-chlorophenyl | |
| 58 | —OCH₃ | -4-tert-butyl | |
| 59 | —OCH₃ | -2-MeO-phenyl | |
| 60 | —OCH₃ | -4-i-Pr—O-phenyl | |
| 61 | —OCH₃ | -2-MeS-phenyl | |
| 62 | —OCH₃ | -2-fluorophenyl | |
| 63 | —OCH₃ | -3-trifluoromethylphenyl | |
| 64 | —OCH₃ | -3,5-dichlorophenyl | |
| 65 | —OCH₃ | -3-phenylphenyl | |
| 66 | —OCH₃ | -4-phenoxyphenyl | |
| 67 | —OCH₃ | -3-CH₃(C=N—OMe)-phenyl | |
| 68 | —OCH₃ | -3-CH₃(C=N—On—Bu)-phenyl | |
| 69 | —OCH₃ | -3-pyridyl | |
| 70 | —OCH₃ | -5-pyrimidinyl | |
| 71 | —OCH₃ | -3-thienyl | |
| 72 | —OCH₃ | -3-indolyl | |
| 73 | —OCH₃ | -5-(4-methylthiazolyl) | |
| 74 | —OCH₃ | -5-indazolyl | |
| 75 | —OCH₃ | -3-(6-chloropyridyl) | |
| 76 | —NHCH₃ | -2-naphthyl | |
| 77 | —NHCH₃ | -n-hexyl | |
| 78 | —NHCH₃ | -cyclohexyl | |
| 79 | —NHCH₃ | -thiophenyl | |
| 80 | —NHCH₃ | -phenyl | |
| 81 | —NHCH₃ | -4-Me-phenyl | |
| 82 | —NHCH₃ | -4-chlorophenyl | |
| 83 | —NHCH₃ | -4-tert-butyl | |
| 84 | —NHCH₃ | -2-MeO-phenyl | |
| 85 | —NHCH₃ | -4-i-Pr—O-phenyl | |
| 86 | —NHCH₃ | -2-MeS-phenyl | |
| 87 | —NHCH₃ | -2-fluorophenyl | |
| 88 | —NHCH₃ | -3-trifluoromethylphenyl | |
| 89 | —NHCH₃ | -3,5-dichlorophenyl | |
| 90 | —NHCH₃ | -3-phenylphenyl | |
| 91 | —NHCH₃ | -4-phenoxyphenyl | |
| 92 | —NHCH₃ | -3-CH₃(C=N—OMe)-phenyl | |
| 93 | —NHCH₃ | -3-CH₃(C=N—On—Bu)-phenyl | |
| 94 | —NHCH₃ | -3-pyridyl | |
| 95 | —NHCH₃ | -5-pyrimidinyl | |
| 96 | —NHCH₃ | -3-thienyl | |
| 97 | —NHCH₃ | -3-indolyl | |
| 98 | —NHCH₃ | -5-(4-methylthiazolyl) | |
| 99 | —NHCH₃ | -5-indazolyl | |
| 100 | —NHCH₃ | -3-(6-chloropyridyl) | |

TABLE 1-continued

| No. | R¹ | R² | Data |
|---|---|---|---|
| 101 | —SCH₃ | -2-naphthyl | |
| 102 | —SCH₃ | -n-hexyl | |
| 103 | —SCH₃ | -cyclohexyl | |
| 104 | —SCH₃ | -thiophenyl | |
| 105 | —SCH₃ | -phenyl | |
| 106 | —SCH₃ | -4-Me-phenyl | |
| 107 | —SCH₃ | -4-chlorophenyl | |
| 108 | —SCH₃ | -4-tert-butyl | |
| 109 | —SCH₃ | -2-MeO-phenyl | |
| 110 | —SCH₃ | -4-i-Pr—O-phenyl | |
| 111 | —SCH₃ | -2-MeS-phenyl | |
| 112 | —SCH₃ | -2-fluorophenyl | |
| 113 | —SCH₃ | -3-trifluoromethylphenyl | |
| 114 | —SCH₃ | -3,5-dichlorophenyl | |
| 115 | —SCH₃ | -3-phenylphenyl | |
| 116 | —SCH₃ | -4-phenoxyphenyl | |
| 117 | —SCH₃ | -3-CH₃(C═N—OMe)-phenyl | |
| 118 | —SCH₃ | -3-CH₃(C═N—On—Bu)-phenyl | |
| 119 | —SCH₃ | -3-pyridyl | |
| 120 | —SCH₃ | -5-pyrimidinyl | |
| 121 | —SCH₃ | -3-thienyl | |
| 122 | —SCH₃ | -3-indolyl | |
| 123 | —SCH₃ | -5-(4-methylthiazolyl) | |
| 124 | —SCH₃ | -5-indazolyl | |
| 125 | —SCH₃ | -3-(6-chloropyridyl) | |
| 126 | —Me | -2-chlorophenyl | |
| 127 | —Me | -2-Me-phenyl | |
| 128 | —Me | -3-chlorophenyl | |
| 129 | —Me | -3-bromophenyl | |
| 130 | —Me | -4-nitrophenyl | |
| 131 | —Me | -tert-butyl | |
| 132 | —Et | -phenyl | |
| 133 | —Et | -4-chlorophenyl | |
| 134 | —Et | -3,5-dichlorophenyl | |
| 135 | —Et | -2-naphthyl | |
| 136 | -cyclopropyl | -phenyl | |
| 137 | -cyclopropyl | -4-chlorophenyl | |
| 138 | -cyclopropyl | -3,5-dichlorophenyl | |
| 139 | -cyclopropyl | -4-CH₃O-phenyl | |
| 140 | -cyclopropyl | -4-tBu-phenyl | |
| 141 | -cyclopropyl | -2-naphthyl | |
| 142 | —CN | -2-chlorophenyl | |
| 143 | —CN | -2-Me-phenyl | |
| 144 | —CN | -4-C(H)═N—O—nBu | |
| 145 | phthalimide N—O structure | | |

The following o-iminooxymethylbenzoyl chlorides IV can be prepared by the processes mentioned.

TABLE 2

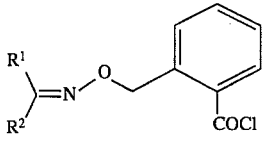

| No. | R¹ | R² | Data |
|---|---|---|---|
| 1 | —CN | -2-naphthyl | |
| 2 | —CN | -n-hexyl | |
| 3 | —CN | -cyclohexyl | |
| 4 | —CN | -thiophenyl | |
| 5 | —CN | -phenyl | |
| 6 | —CN | -4-Me-phenyl | |
| 7 | —CN | -4-chlorophenyl | |
| 8 | —CN | -4-tert-butyl | |
| 9 | —CN | -2-MeO-phenyl | |
| 10 | —CN | -4-i-Pr—O-phenyl | |
| 11 | —CN | -2-MeS-phenyl | |
| 12 | —CN | -2-fluorophenyl | |
| 13 | —CN | -3-trifluoromethylphenyl | |
| 14 | —CN | -3,5-dichlorophenyl | |
| 15 | —CN | -3-phenylphenyl | |
| 16 | —CN | -4-phenoxyphenyl | |
| 17 | —CN | -3-CH₃(C=N—OMe)-phenyl | |
| 18 | —CN | -3-CH₃(C=N—On—Bu)-phenyl | |
| 19 | —CN | -3-pyridyl | |
| 20 | —CN | -5-pyrimidinyl | |
| 21 | —CN | -3-thienyl | |
| 22 | —CN | -3-indolyl | |
| 23 | —CN | -5-(4-methylthiazolyl) | |
| 24 | —CN | -5-indazolyl | |
| 25 | —CN | -3-(6-chloropyridyl) | |
| 26 | —CH₃ | -2-naphthyl | |
| 27 | —CH₃ | -n-hexyl | |
| 28 | —CH₃ | -cyclohexyl | |
| 29 | —CH₃ | -thiophenyl | |
| 30 | —CH₃ | -phenyl | |
| 31 | —CH₃ | -4-Me-phenyl | NMR (CDCl₃/TMS) 2.35(s, 6H); 5.70 (s, 2H); 7.10–8.15 (m, 8H) |
| 32 | —CH₃ | -4-chlorophenyl | |
| 33 | —CH₃ | -4-tert-butyl | |
| 34 | —CH₃ | -2-MeO-phenyl | |
| 35 | —CH₃ | -4-i-Pr—O-phenyl | |
| 36 | —CH₃ | -2-MeS-phenyl | |
| 37 | —CH₃ | -2-fluorophenyl | |
| 38 | —CH₃ | -3-trifluoromethylphenyl | |
| 39 | —CH₃ | -3,5-dichlorophenyl | |
| 40 | —CH₃ | -3-phenylphenyl | |
| 41 | —CH₃ | -4-phenoxyphenyl | |
| 42 | —CH₃ | -3-CH₃(C=N—OMe)-phenyl | |
| 43 | —CH₃ | -3-CH₃(C=N—On—Bu)-phenyl | |
| 44 | —CH₃ | -3-pyridyl | |
| 45 | —CH₃ | -5-pyrimidinyl | |
| 46 | —CH₃ | -3-thienyl | |
| 47 | —CH₃ | -3-indolyl | |
| 48 | —CH₃ | -5-(4-methylthiazolyl) | |
| 49 | —CH₃ | -5-indazolyl | |
| 50 | —CH₃ | -3-(6-chloropyridyl) | |
| 51 | —OCH₃ | -2-naphthyl | |
| 52 | —OCH₃ | -n-hexyl | |
| 53 | —OCH₃ | -cyclohexyl | |
| 54 | —OCH₃ | -thiophenyl | |
| 55 | —OCH₃ | -phenyl | |
| 56 | —OCH₃ | -4-Me-phenyl | |
| 57 | —OCH₃ | -4-chlorophenyl | |
| 58 | —OCH₃ | -4-tert-butyl | |
| 59 | —OCH₃ | -2-MeO-phenyl | |
| 60 | —OCH₃ | -4-i-Pr—O-phenyl | |
| 61 | —OCH₃ | -2-MeS-phenyl | |
| 62 | —OCH₃ | -2-fluorophenyl | |
| 63 | —OCH₃ | -3-trifluoromethylphenyl | |
| 64 | —OCH₃ | -3,5-dichlorophenyl | |
| 65 | —OCH₃ | -3-phenylphenyl | |
| 66 | —OCH₃ | -4-phenoxyphenyl | |
| 67 | —OCH₃ | -3-CH₃(C=N—OMe)-phenyl | |

TABLE 2-continued

Structure IV: R¹R²C=N-O-CH₂-(phenyl with COCl at ortho position)

| No. | R¹ | R² | Data |
|---|---|---|---|
| 68 | —OCH₃ | -3-CH₃(C=N—On—Bu)-phenyl | |
| 69 | —OCH₃ | -3-pyridyl | |
| 70 | —OCH₃ | -5-pyrimidinyl | |
| 71 | —OCH₃ | -3-thienyl | |
| 72 | —OCH₃ | -3-indolyl | |
| 73 | —OCH₃ | -5-(4-methylthiazolyl) | |
| 74 | —OCH₃ | -5-indazolyl | |
| 75 | —OCH₃ | -3-(6-chloropyridyl) | |
| 76 | —NHCH₃ | -2-naphthyl | |
| 77 | —NHCH₃ | -n-hexyl | |
| 78 | —NHCH₃ | -cyclohexyl | |
| 79 | —NHCH₃ | -thiophenyl | |
| 80 | —NHCH₃ | -phenyl | |
| 81 | —NHCH₃ | -4-Me-phenyl | |
| 82 | —NHCH₃ | -4-chlorophenyl | |
| 83 | —NHCH₃ | -4-tert-butyl | |
| 84 | —NHCH₃ | -2-MeO-phenyl | |
| 85 | —NHCH₃ | -4-i-Pr—O-phenyl | |
| 86 | —NHCH₃ | -2-MeS-phenyl | |
| 87 | —NHCH₃ | -2-fluorophenyl | |
| 88 | —NHCH₃ | -3-trifluoromethylphenyl | |
| 89 | —NHCH₃ | -3,5-dichlorophenyl | |
| 90 | —NHCH₃ | -3-phenylphenyl | |
| 91 | —NHCH₃ | -4-phenoxyphenyl | |
| 92 | —NHCH₃ | -3-CH₃(C=N—OMe)-phenyl | |
| 93 | —NHCH₃ | -3-CH₃(C=N—On—Bu)-phenyl | |
| 94 | —NHCH₃ | -3-pyridyl | |
| 95 | —NHCH₃ | -5-pyrimidinyl | |
| 96 | —NHCH₃ | -3-thienyl | |
| 97 | —NHCH₃ | -3-indolyl | |
| 98 | —NHCH₃ | -5-(4-methylthiazolyl) | |
| 99 | —NHCH₃ | -5-indazolyl | |
| 100 | —NHCH₃ | -3-(6-chloropyridyl) | |
| 101 | —SCH₃ | -2-naphthyl | |
| 102 | —SCH₃ | -n-hexyl | |
| 103 | —SCH₃ | -cyclohexyl | |
| 104 | —SCH₃ | -thiophenyl | |
| 105 | —SCH₃ | -phenyl | |
| 106 | —SCH₃ | -4-Me-phenyl | |
| 107 | —SCH₃ | -4-chlorophenyl | |
| 108 | —SCH₃ | -4-tert-butyl | |
| 109 | —SCH₃ | -2-MeO-phenyl | |
| 110 | —SCH₃ | -4-i-Pr—O-phenyl | |
| 111 | —SCH₃ | -2-MeS-phenyl | |
| 112 | —SCH₃ | -2-fluorophenyl | |
| 113 | —SCH₃ | -3-trifluoromethylphenyl | |
| 114 | —SCH₃ | -3,5-dichlorophenyl | |
| 115 | —SCH₃ | -3-phenylphenyl | |
| 116 | —SCH₃ | -4-phenoxyphenyl | |
| 117 | —SCH₃ | -3-CH₃(C=N—OMe)-phenyl | |
| 118 | —SCH₃ | -3-CH₃(C=N—On—Bu)-phenyl | |
| 119 | —SCH₃ | -3-pyridyl | |
| 120 | —SCH₃ | -5-pyrimidinyl | |
| 121 | —SCH₃ | -3-thienyl | |
| 122 | —SCH₃ | -3-indolyl | |
| 123 | —SCH₃ | -5-(4-methylthiazolyl) | |
| 124 | —SCH₃ | -5-indazolyl | |
| 125 | —SCH₃ | -3-(6-chloropyridyl) | |
| 126 | —Me | -2-chlorophenyl | |
| 127 | —Me | -2-Me-phenyl | |
| 128 | —Me | -3-chlorophenyl | |
| 129 | —Me | -3-bromophenyl | |
| 130 | —Me | -4-nitrophenyl | |
| 131 | —Me | -tert-butyl | |
| 132 | —Et | -phenyl | |
| 133 | —Et | -4-chlorophenyl | |
| 134 | —Et | -3,5-dichlorophenyl | |
| 135 | —Et | -2-naphthyl | |
| 136 | -cyclopropyl | -phenyl | |
| 137 | -cyclopropyl | -4-chlorophenyl | |

TABLE 2-continued

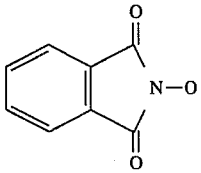

IV

| No. | R¹ | R² | Data |
|---|---|---|---|
| 138 | -cyclopropyl | -3,5-dichlorophenyl | |
| 139 | -cyclopropyl | -4-CH₃O-phenyl | |
| 140 | -cyclopropyl | -4-tBu-phenyl | |
| 141 | -cyclopropyl | -2-naphthyl | |
| 142 | —CN | -2-chlorophenyl | |
| 143 | —CN | -2-Me-phenyl | |
| 144 | —CN | -4-C(H)=N—O—nBu | |
| 145 | phthalimide N—O | | |

The following o-iminooxymethylbenzoyl cyanides VI can be prepared, for example, by the processes mentioned.

TABLE 3

VI

| No. | R¹ | R² | Data |
|---|---|---|---|
| 1 | —CN | -2-naphthyl | |
| 2 | —CN | -n-hexyl | |
| 3 | —CN | -cyclohexyl | |
| 4 | —CN | -thiophenyl | |
| 5 | —CN | -phenyl | |
| 6 | —CN | -4-Me-phenyl | |
| 7 | —CN | -4-chlorophenyl | |
| 8 | —CN | -4-tert-butyl | |
| 9 | —CN | -2-MeO-phenyl | |
| 10 | —CN | -4-i-Pr—O-phenyl | |
| 11 | —CN | -2-MeS-phenyl | |
| 12 | —CN | -2-fluorophenyl | |
| 13 | —CN | -3-trifluoromethylphenyl | |
| 14 | —CN | -3,5-dichlorophenyl | |
| 15 | —CN | -3-phenylphenyl | |
| 16 | —CN | -4-phenoxyphenyl | |
| 17 | —CN | -3-CH₃(C=N—OMe)-phenyl | |
| 18 | —CN | -3-CH₃(C=N—On—Bu)-phenyl | |
| 19 | —CN | -3-pyridyl | |
| 20 | —CN | -5-pyrimidinyl | |
| 21 | —CN | -3-thienyl | |
| 22 | —CN | -3-indolyl | |
| 23 | —CN | -5-(4-methylthiazolyl) | |
| 24 | —CN | -5-indazolyl | |
| 25 | —CN | -3-(6-chloropyridyl) | |
| 26 | —CH₃ | -2-naphthyl | |
| 27 | —CH₃ | -n-hexyl | |
| 28 | —CH₃ | -cyclohexyl | |
| 29 | —CH₃ | -thiophenyl | |
| 30 | —CH₃ | -phenyl | |
| 31 | —CH₃ | -4-Me-phenyl | |
| 32 | —CH₃ | -4-chlorophenyl | |
| 33 | —CH₃ | -4-tert-butyl | |
| 34 | —CH₃ | -2-MeO-phenyl | |
| 35 | —CH₃ | -4-i-Pr—O-phenyl | |

TABLE 3-continued

VI

| No. | R¹ | R² | Data |
|---|---|---|---|
| 36 | —CH₃ | -2-MeS-Phenyl | |
| 37 | —CH₃ | -2-fluorophenyl | |
| 38 | —CH₃ | -3-trifluoromethylphenyl | |
| 39 | —CH₃ | -3,5-dichlorophenyl | |
| 40 | —CH₃ | -3-phenylphenyl | |
| 41 | —CH₃ | -4-phenoxyphenyl | |
| 42 | —CH₃ | -3-CH₃(C=N—OMe)-phenyl | |
| 43 | —CH₃ | -3-CH₃(C=N—On—Bu)-phenyl | |
| 44 | —CH₃ | -3-pyridyl | |
| 45 | —CH₃ | -5-pyrimidinyl | |
| 46 | —CH₃ | -3-thienyl | |
| 47 | —CH₃ | -3-indolyl | |
| 48 | —CH₃ | -5-(4-methylthiazolyl) | |
| 49 | —CH₃ | -5-indazolyl | |
| 50 | —CH₃ | -3-(6-chloropyridyl) | |
| 51 | —OCH₃ | -2-naphthyl | |
| 52 | —OCH₃ | -n-hexyl | |
| 53 | —OCH₃ | -cyclohexyl | |
| 54 | —OCH₃ | -thiophenyl | |
| 55 | —OCH₃ | -phenyl | |
| 56 | —OCH₃ | -4-Me-phenyl | |
| 57 | —OCH₃ | -4-chlorophenyl | |
| 58 | —OCH₃ | -4-tert-butyl | |
| 59 | —OCH₃ | -2-MeO-phenyl | |
| 60 | —OCH₃ | -4-i-Pr—O-phenyl | |
| 61 | —OCH₃ | -2-MeS-phenyl | |
| 62 | —OCH₃ | -2-fluorophenyl | |
| 63 | —OCH₃ | -3-trifluoromethylphenyl | |
| 64 | —OCH₃ | -3,5-dichlorophenyl | |
| 65 | —OCH₃ | -3-phenylphenyl | |
| 66 | —OCH₃ | -4-phenoxyphenyl | |
| 67 | —OCH₃ | -3-CH₃(C=N—OMe)-phenyl | |
| 68 | —OCH₃ | -3-CH₃(C=N—On—Bu)-phenyl | |
| 69 | —OCH₃ | -3-pyridyl | |
| 70 | —OCH₃ | -5-pyrimidinyl | |
| 71 | —OCH₃ | -3-thienyl | |
| 72 | —OCH₃ | -3-indolyl | |
| 73 | —OCH₃ | -5-(4-methylthiazolyl) | |
| 74 | —OCH₃ | -5-indazolyl | |
| 75 | —OCH₃ | -3-(6-chloropyridyl) | |
| 76 | —NHCH₃ | -2-naphthyl | |
| 77 | —NHCH₃ | -n-hexyl | |
| 78 | —NHCH₃ | -cyclohexyl | |
| 79 | —NHCH₃ | -thiophenyl | |
| 80 | —NHCH₃ | -phenyl | |
| 81 | —NHCH₃ | -4-Me-phenyl | |
| 82 | —NHCH₃ | -4-chlorophenyl | |
| 83 | —NHCH₃ | -4-tert-butyl | |
| 84 | —NHCH₃ | -2-MeO-phenyl | |
| 85 | —NHCH₃ | -4-i-Pr—O-phenyl | |
| 86 | —NHCH₃ | -2-MeS-phenyl | |
| 87 | —NHCH₃ | -2-fluorophenyl | |
| 88 | —NHCH₃ | -3-trifluoromethylphenyl | |
| 89 | —NHCH₃ | -3,5-dichlorophenyl | |
| 90 | —NHCH₃ | -3-phenylphenyl | |
| 91 | —NHCH₃ | -4-phenoxyphenyl | |
| 92 | —NHCH₃ | -3-CH₃(C=N—OMe)-phenyl | |
| 93 | —NHCH₃ | -3-CH₃(C=N—On—Bu)-phenyl | |
| 94 | —NHCH₃ | -3-pyridyl | |
| 95 | —NHCH₃ | -5-pyrimidinyl | |
| 96 | —NHCH₃ | -3-thienyl | |
| 97 | —NHCH₃ | -3-indolyl | |
| 98 | —NHCH₃ | -5-(4-methylthiazolyl) | |
| 99 | —NHCH₃ | -5-indazolyl | |
| 100 | —NHCH₃ | -3-(6-chloropyridyl) | |
| 101 | —SCH₃ | -2-naphthyl | |
| 102 | —SCH₃ | -n-hexyl | |
| 103 | —SCH₃ | -cyclohexyl | |
| 104 | —SCH₃ | -thiophenyl | |

TABLE 3-continued

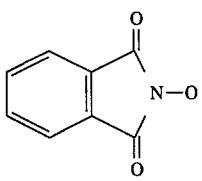

| No. | R¹ | R² | Data |
|---|---|---|---|
| 105 | —SCH₃ | -phenyl | |
| 106 | —SCH₃ | -4-Me-phenyl | |
| 107 | —SCH₃ | -4-chlorophenyl | |
| 108 | —SCH₃ | -4-tert-butyl | |
| 109 | —SCH₃ | -2-MeO-phenyl | |
| 110 | —SCH₃ | -4-i-Pr—O-phenyl | |
| 111 | —SCH₃ | -2-MeS-phenyl | |
| 112 | —SCH₃ | -2-fluorophenyl | |
| 113 | —SCH₃ | -3-trifluoromethylphenyl | |
| 114 | —SCH₃ | -3,5-dichlorophenyl | |
| 115 | —SCH₃ | -3-phenylphenyl | |
| 116 | —SCH₃ | -4-phenoxyphenyl | |
| 117 | —SCH₃ | -3-CH₃(C=N—OMe)-phenyl | |
| 118 | —SCH₃ | -3-CH₃(C=N—On—Bu)-phenyl | |
| 119 | —SCH₃ | -3-pyridyl | |
| 120 | —SCH₃ | -5-pyrimidinyl | |
| 121 | —SCH₃ | -3-thienyl | |
| 122 | —SCH₃ | -3-indolyl | |
| 123 | —SCH₃ | -5-(4-methylthiazolyl) | |
| 124 | —SCH₃ | -5-indazolyl | |
| 125 | —SCH₃ | -3-(6-chloropyridyl) | |
| 126 | —Me | -2-chlorophenyl | |
| 127 | —Me | -2-Me-phenyl | |
| 128 | —Me | -3-chlorophenyl | |
| 129 | —Me | -3-bromophenyl | |
| 130 | —Me | -4-nitrophenyl | |
| 131 | —Me | -tert-butyl | |
| 132 | —Et | -phenyl | |
| 133 | —Et | -4-chlorophenyl | |
| 134 | —Et | -3,5-dichlorophenyl | |
| 135 | —Et | -2-naphthyl | |
| 136 | -cyclopropyl | -phenyl | |
| 137 | -cyclopropyl | -4-chlorophenyl | |
| 138 | -cyclopropyl | -3,5-dichlorophenyl | |
| 139 | -cyclopropyl | -4-CH₃O-phenyl | |
| 140 | -cyclopropyl | -4-tBu-phenyl | |
| 141 | -cyclopropyl | -2-naphthyl | |
| 142 | —CN | -2-chlorophenyl | |
| 143 | —CN | -2-Me-phenyl | |
| 144 | —CN | -4-C(H)=N—O—nBu | |
| 145 | | | |

The following methyl o-iminooxymethylphenylglyoxylates VIII can be prepared, for example, by the processes mentioned.

TABLE 4

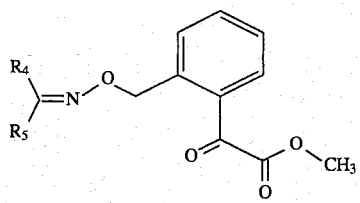

VIII

| No. | R⁵ | R⁴ | Data |
|---|---|---|---|
| 1 | —CN | -2-naphthyl | |
| 2 | —CN | -n-hexyl | |
| 3 | —CN | -cyclohexyl | |
| 4 | —CN | -thiophenyl | |
| 5 | —CN | -phenyl | |
| 6 | —CN | -4-Me-phenyl | |
| 7 | —CN | -4-chlorophenyl | |
| 8 | —CN | -4-tert-butyl | |
| 9 | —CN | -2-MeO-phenyl | |
| 10 | —CN | -4-i-Pr—O-phenyl | |
| 11 | —CN | -2-MeS-phenyl | |
| 12 | —CN | -2-fluorophenyl | |
| 13 | —CN | -3-trifluoromethylphenyl | |
| 14 | —CN | -3,5-dichlorophenyl | |
| 15 | —CN | -3-phenylphenyl | |
| 16 | —CN | -4-phenoxyphenyl | |
| 17 | —CN | -3-CH₃(C=N—OMe)-phenyl | |
| 18 | —CN | -3-CH₃(C=N—On—Bu)-phenyl | |
| 19 | —CN | -3-pyridyl | |
| 20 | —CN | -5-pyrimidinyl | |
| 21 | —CN | -3-thienyl | |
| 22 | —CN | -3-indolyl | |
| 23 | —CN | -5-(4-methylthiazolyl) | |
| 24 | —CN | -5-indazolyl | |
| 25 | —CN | -3-(6-chloropyridyl) | |
| 26 | —CH₃ | -2-naphthyl | |
| 27 | —CH₃ | -n-hexyl | |
| 28 | —CH₃ | -cyclohexyl | |
| 29 | —CH₃ | -thiophenyl | |
| 30 | —CH₃ | -phenyl | |
| 31 | —CH₃ | -4-Me-phenyl | IR: 1738; 1687; 1206; 1011; 818 cm⁻¹ |
| 32 | —CH₃ | -4-chlorophenyl | |
| 33 | —CH₃ | -4-tert-butyl | |
| 34 | —CH₃ | -2-MeO-phenyl | |
| 35 | —CH₃ | -4-i-Pr—O-phenyl | |
| 36 | —CH₃ | -2-MeS-phenyl | |
| 37 | —CH₃ | -2-fluorophenyl | |
| 38 | —CH₃ | -3-trifluoromethylphenyl | |
| 39 | —CH₃ | -3,5-dichlorophenyl | |
| 40 | —CH₃ | -3-phenylphenyl | |
| 41 | —CH₃ | -4-phenoxyphenyl | |
| 42 | —CH₃ | -3-CH₃(C=N—OMe)-phenyl | |
| 43 | —CH₃ | -3-CH₃(C=N—On—Bu)-phenyl | |
| 44 | —CH₃ | -3-pyridyl | |
| 45 | —CH₃ | -5-pyrimidinyl | |
| 46 | —CH₃ | -3-thienyl | |
| 47 | —CH₃ | -3-indolyl | |
| 48 | —CH₃ | -5-(4-methylthiazolyl) | |
| 49 | —CH₃ | -5-indazolyl | |
| 50 | —CH₃ | -3-(6-chloropyridyl) | |
| 51 | —OCH₃ | -2-naphthyl | |
| 52 | —OCH₃ | -n-hexyl | |
| 53 | —OCH₃ | -cyclohexyl | |
| 54 | —OCH₃ | -thiophenyl | |
| 55 | —OCH₃ | -phenyl | |
| 56 | —OCH₃ | -4-Me-phenyl | |
| 57 | —OCH₃ | -4-chlorophenyl | |
| 58 | —OCH₃ | -4-tert-butyl | |
| 59 | —OCH₃ | -2-MeO-phenyl | |
| 60 | —OCH₃ | -4-i-Pr—O-phenyl | |
| 61 | —OCH₃ | -2-MeS-phenyl | |
| 62 | —OCH₃ | -2-fluorophenyl | |
| 63 | —OCH₃ | -3-trifluoromethylphenyl | |
| 64 | —OCH₃ | -3,5-dichlorophenyl | |
| 65 | —OCH₃ | -3-phenylphenyl | |

TABLE 4-continued

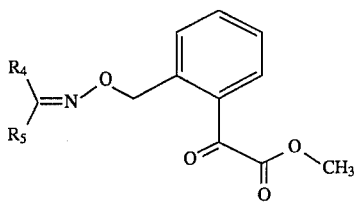

VIII

| No. | R⁵ | R⁴ | Data |
|---|---|---|---|
| 66 | —OCH₃ | -4-phenoxyphenyl | |
| 67 | —OCH₃ | -3-CH₃(C=N—OMe)-phenyl | |
| 68 | —OCH₃ | -3-CH₃(C=N—On—Bu)-phenyl | |
| 69 | —OCH₃ | -3-pyridyl | |
| 70 | —OCH₃ | -5-pyrimidinyl | |
| 71 | —OCH₃ | -3-thienyl | |
| 72 | —OCH₃ | -3-indolyl | |
| 73 | —OCH₃ | -5-(4-methylthiazolyl) | |
| 74 | —OCH₃ | -5-indazolyl | |
| 75 | —OCH₃ | -3-(6-chloropyridyl) | |
| 76 | —NHCH₃ | -2-naphthyl | |
| 77 | —NHCH₃ | -n-hexyl | |
| 78 | —NHCH₃ | -cyclohexyl | |
| 79 | —NHCH₃ | -thiophenyl | |
| 80 | —NHCH₃ | -phenyl | |
| 81 | —NHCH₃ | -4-Me-phenyl | |
| 82 | —NHCH₃ | -4-chlorophenyl | |
| 83 | —NHCH₃ | -4-tert-butyl | |
| 84 | —NHCH₃ | -2-MeO-phenyl | |
| 85 | —NHCH₃ | -4-i-Pr—O-phenyl | |
| 86 | —NHCH₃ | -2-MeS-phenyl | |
| 87 | —NHCH₃ | -2-fluorophenyl | |
| 88 | —NHCH₃ | -3-trifluoromethylphenyl | |
| 89 | —NHCH₃ | -3,5-dichlorophenyl | |
| 90 | —NHCH₃ | -3-phenylphenyl | |
| 91 | —NHCH₃ | -4-phenoxyphenyl | |
| 92 | —NHCH₃ | -3-CH₃(C=N—OMe)-phenyl | |
| 93 | —NHCH₃ | -3-CH₃(C=N—On—Bu)-phenyl | |
| 94 | —NHCH₃ | -3-pyridyl | |
| 95 | —NHCH₃ | -5-pyrimidinyl | |
| 96 | —NHCH₃ | -3-thienyl | |
| 97 | —NHCH₃ | -3-indolyl | |
| 98 | —NHCH₃ | -5-(4-methylthiazolyl) | |
| 99 | —NHCH₃ | -5-indazolyl | |
| 100 | —NHCH₃ | -3-(6-chloropyridyl) | |
| 101 | —SCH₃ | -2-naphthyl | |
| 102 | —SCH₃ | -n-hexyl | |
| 103 | —SCH₃ | -cyclohexyl | |
| 104 | —SCH₃ | -thiophenyl | |
| 105 | —SCH₃ | -phenyl | |
| 106 | —SCH₃ | -4-Me-phenyl | |
| 107 | —SCH₃ | -4-chlorophenyl | |
| 108 | —SCH₃ | -4-tert-butyl | |
| 109 | —SCH₃ | -2-MeO-phenyl | |
| 110 | —SCH₃ | -4-i-Pr—O-phenyl | |
| 111 | —SCH₃ | -2-MeS-phenyl | |
| 112 | —SCH₃ | -2-fluorophenyl | |
| 113 | —SCH₃ | -3-trifluoromethylphenyl | |
| 114 | —SCH₃ | -3,5-dichlorophenyl | |
| 115 | —SCH₃ | -3-phenylphenyl | |
| 116 | —SCH₃ | -4-phenoxyphenyl | |
| 117 | —SCH₃ | -3-CH₃(C=N—OMe)-phenyl | |
| 118 | —SCH₃ | -3-CH₃(C=N—On—Bu)-phenyl | |
| 119 | —SCH₃ | -3-pyridyl | |
| 120 | —SCH₃ | -5-pyrimidinyl | |
| 121 | —SCH₃ | -3-thienyl | |
| 122 | —SCH₃ | -3-indolyl | |
| 123 | —SCH₃ | -5-(4-methylthiazolyl) | |
| 124 | —SCH₃ | -5-indazolyl | |
| 125 | —SCH₃ | -3-(6-chloropyridyl) | |
| 126 | —Me | -2-chlorophenyl | |
| 127 | —Me | -2-Me-phenyl | |
| 128 | —Me | -3-chlorophenyl | |
| 129 | —Me | -3-bromophenyl | |
| 130 | —Me | -4-nitrophenyl | |
| 131 | —Me | -tert-butyl | |
| 132 | —Et | -phenyl | |

TABLE 4-continued

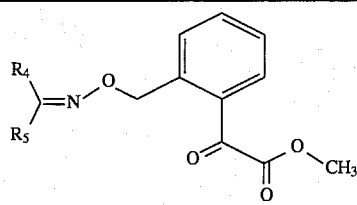

VIII

| No. | R⁵ | R⁴ | Data |
|---|---|---|---|
| 133 | —Et | -4-chlorophenyl | |
| 134 | —Et | -3,5-dichlorophenyl | |
| 135 | —Et | -2-naphthyl | |
| 136 | -cyclopropyl | -phenyl | |
| 137 | -cyclopropyl | -4-chlorophenyl | |
| 138 | -cyclopropyl | -3,5-dichlorophenyl | |
| 139 | -cyclopropyl | -4-CH₃O-phenyl | |
| 140 | -cyclopropyl | -4-tBu-phenyl | |
| 141 | -cyclopropyl | -2-naphthyl | |
| 142 | —CN | -2-chlorophenyl | |
| 143 | —CN | -2-Me-phenyl | |
| 144 | —CN | -4-C(H)=N—O—nBu | |

145

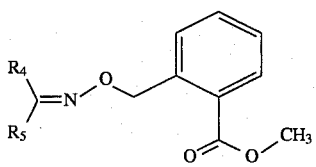

The following o-iminooxymethylbenzoic acid esters V can be prepared, for example, by the processes mentioned.

TABLE 5

V

| No. | R⁵ | R⁴ | Data |
|---|---|---|---|
| 1 | —CN | -2-naphthyl | |
| 2 | —CN | -n-hexyl | |
| 3 | —CN | -cyclohexyl | |
| 4 | —CN | -thiophenyl | |
| 5 | —CN | -phenyl | |
| 6 | —CN | -4-Me-phenyl | |
| 7 | —CN | -4-chlorophenyl | |
| 8 | —CN | -4-tert-butyl | |
| 9 | —CN | -2-MeO-phenyl | |
| 10 | —CN | -4-i-Pr—O-phenyl | |
| 11 | —CN | -2-MeS-phenyl | |
| 12 | —CN | -2-fluorophenyl | |
| 13 | —CN | -3-trifluoromethylphenyl | |
| 14 | —CN | -3,5-dichlorophenyl | |
| 15 | —CN | -3-phenylphenyl | |
| 16 | —CN | -4-phenoxyphenyl | |
| 17 | —CN | -3-CH₃(C=N—OMe)-phenyl | |
| 18 | —CN | -3-CH₃(C=N—On—Bu)-phenyl | |
| 19 | —CN | -3-pyridyl | |
| 20 | —CN | -5-pyrimidinyl | |
| 21 | —CN | -3-thienyl | |
| 22 | —CN | -3-indolyl | |
| 23 | —CN | -5-(4-methylthiazolyl) | |
| 24 | —CN | -5-indazolyl | |
| 25 | —CN | -3-(6-chloropyridyl) | |
| 26 | —CH₃ | -2-naphthyl | |
| 27 | —CH₃ | -n-hexyl | |

TABLE 5-continued

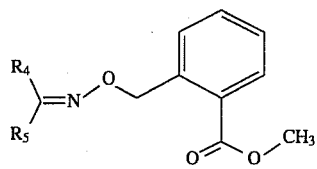

V

| No. | R⁵ | R⁴ | Data |
|---|---|---|---|
| 28 | —CH₃ | -cyclohexyl | |
| 29 | —CH₃ | -thiophenyl | |
| 30 | —CH₃ | -phenyl | |
| 31 | —CH₃ | -4-Me-phenyl | IR: 1719; 1261; 1136; 1040; 738 cm⁻¹ |
| 32 | —CH₃ | -4-chlorophenyl | NMR: 2.30(s, 3H); 3.90(s, 3H); 5.65 (s, 2H); 8.05–7.25 (m, 8H) |
| 33 | —CH₃ | -4-tert-butyl | |
| 34 | —CH₃ | -2-MeO-phenyl | |
| 35 | —CH₃ | -4-i-Pr—O-phenyl | |
| 36 | —CH₃ | -2-MeS-phenyl | |
| 37 | —CH₃ | -2-fluorophenyl | |
| 38 | —CH₃ | -3-trifluoromethylphenyl | |
| 39 | —CH₃ | -3,5-dichlorophenyl | |
| 40 | —CH₃ | -3-phenylphenyl | |
| 41 | —CH₃ | -4-phenoxyphenyl | |
| 42 | —CH₃ | -3-CH₃(C=N—OMe)-phenyl | |
| 43 | —CH₃ | -3-CH₃(C=N—On—Bu)-phenyl | |
| 44 | —CH₃ | -3-pyridyl | |
| 45 | —CH₃ | -5-pyrimidinyl | |
| 46 | —CH₃ | -3-thienyl | |
| 47 | —CH₃ | -3-indolyl | |
| 48 | —CH₃ | -5-(4-methylthiazolyl) | |
| 49 | —CH₃ | -5-indazolyl | |
| 50 | —CH₃ | -3-(6-chloropyridyl) | |
| 51 | —OCH₃ | -2-naphthyl | |
| 52 | —OCH₃ | -n-hexyl | |
| 53 | —OCH₃ | -cyclohexyl | |
| 54 | —OCH₃ | -thiophenyl | |
| 55 | —OCH₃ | -phenyl | |
| 56 | —OCH₃ | -4-Me-phenyl | |
| 57 | —OCH₃ | -4-chlorophenyl | |
| 58 | —OCH₃ | -4-tert-butyl | |
| 59 | —OCH₃ | -2-MeO-phenyl | |
| 60 | —OCH₃ | -4-i-Pr—O-phenyl | |
| 61 | —OCH₃ | -2-MeS-phenyl | |
| 62 | —OCH₃ | -2-fluorophenyl | |
| 63 | —OCH₃ | -3-trifluoromethylphenyl | |
| 64 | —OCH₃ | -3,5-dichlorophenyl | |
| 65 | —OCH₃ | -3-phenylphenyl | |
| 66 | —OCH₃ | -4-phenoxyphenyl | |
| 67 | —OCH₃ | -3-CH₃(C=N—OMe)-phenyl | |
| 68 | —OCH₃ | -3-CH₃(C=N—On—Bu)-phenyl | |
| 69 | —OCH₃ | -3-pyridyl | |
| 70 | —OCH₃ | -5-pyrimidinyl | |
| 71 | —OCH₃ | -3-thienyl | |
| 72 | —OCH₃ | -3-indolyl | |
| 73 | —OCH₃ | -5-(4-methylthiazolyl) | |
| 74 | —OCH₃ | -5-indazolyl | |
| 75 | —OCH₃ | -3-(6-chloropyridyl) | |
| 76 | —NHCH₃ | -2-naphthyl | |
| 77 | —NHCH₃ | -n-hexyl | |
| 78 | —NHCH₃ | -cyclohexyl | |
| 79 | —NHCH₃ | -thiophenyl | |
| 80 | —NHCH₃ | -phenyl | |
| 81 | —NHCH₃ | -4-Me-phenyl | |
| 82 | —NHCH₃ | -4-chlorophenyl | |
| 83 | —NHCH₃ | -4-tert-butyl | |
| 84 | —NHCH₃ | -2-MeO-phenyl | |
| 85 | —NHCH₃ | -4-i-Pr—O-phenyl | |
| 86 | —NHCH₃ | -2-MeS-phenyl | |
| 87 | —NHCH₃ | -2-fluorophenyl | |
| 88 | —NHCH₃ | -3-trifluoromethylphenyl | |
| 89 | —NHCH₃ | -3,5-dichlorophenyl | |
| 90 | —NHCH₃ | -3-phenylphenyl | |
| 91 | —NHCH₃ | -4-phenoxyphenyl | |

TABLE 5-continued

V structure: R4R5C=N-O-CH2-(2-position of phenyl), phenyl with -C(=O)-O-CH3

| No. | R⁵ | R⁴ | Data |
|---|---|---|---|
| 92 | —NHCH₃ | -3-CH₃(C=N—OMe)-phenyl | |
| 93 | —NHCH₃ | -3-CH₃(C=N—On—Bu)-phenyl | |
| 94 | —NHCH₃ | -3-pyridyl | |
| 95 | —NHCH₃ | -5-pyrimidinyl | |
| 96 | —NHCH₃ | -3-thienyl | |
| 97 | —NHCH₃ | -3-indolyl | |
| 98 | —NHCH₃ | -5-(4-methylthiazolyl) | |
| 99 | —NHCH₃ | -5-indazolyl | |
| 100 | —NHCH₃ | -3-(6-chloropyridyl) | |
| 101 | —SCH₃ | -2-naphthyl | |
| 102 | —SCH₃ | -n-hexyl | |
| 103 | —SCH₃ | -cyclohexyl | |
| 104 | —SCH₃ | -thiophenyl | |
| 105 | —SCH₃ | -phenyl | |
| 106 | —SCH₃ | -4-Me-phenyl | |
| 107 | —SCH₃ | -4-chlorophenyl | |
| 108 | —SCH₃ | -4-tert-butyl | |
| 109 | —SCH₃ | -2-MeO-phenyl | |
| 110 | —SCH₃ | -4-i-Pr—O-phenyl | |
| 111 | —SCH₃ | -2-MeS-phenyl | |
| 112 | —SCH₃ | -2-fluorophenyl | |
| 113 | —SCH₃ | -3-trifluoromethylphenyl | |
| 114 | —SCH₃ | -3,5-dichlorophenyl | |
| 115 | —SCH₃ | -3-phenylphenyl | |
| 116 | —SCH₃ | -4-phenoxyphenyl | |
| 117 | —SCH₃ | -3-CH₃(C=N—OMe)-phenyl | |
| 118 | —SCH₃ | -3-CH₃(C=N—On—Bu)-phenyl | |
| 119 | —SCH₃ | -3-pyridyl | |
| 120 | —SCH₃ | -5-pyrimidinyl | |
| 121 | —SCH₃ | -3-thienyl | |
| 122 | —SCH₃ | -3-indolyl | |
| 123 | —SCH₃ | -5-(4-methylthiazolyl) | |
| 124 | —SCH₃ | -5-indazolyl | |
| 125 | —SCH₃ | -3-(6-chloropyridyl) | |
| 126 | —Me | -2-chlorophenyl | |
| 127 | —Me | -2-Me-phenyl | |
| 128 | —Me | -3-chlorophenyl | |
| 129 | —Me | -3-bromophenyl | |
| 130 | —Me | -4-nitrophenyl | |
| 131 | —Me | -tert-butyl | |
| 132 | —Et | -phenyl | |
| 133 | —Et | -4-chlorophenyl | |
| 134 | —Et | -3,5-dichlorophenyl | |
| 135 | —Et | -2-naphthyl | |
| 136 | -cyclopropyl | -phenyl | |
| 137 | -cyclopropyl | -4-chlorophenyl | |
| 138 | -cyclopropyl | -3,5-dichlorophenyl | |
| 139 | -cyclopropyl | -4-CH₃O-phenyl | |
| 140 | -cyclopropyl | -4-tBu-phenyl | |
| 141 | -cyclopropyl | -2-naphthyl | |
| 142 | —CN | -2-chlorophenyl | |
| 143 | —CN | -2-Me-phenyl | |
| 144 | —CN | -4-C(H)=N—O—nBu | |
| 145 | phthalimide N—O structure | | |

The following o-iminooxymethylphenyl ketosulfoxides VII can be prepared, for example, by the processes mentioned.

TABLE 6

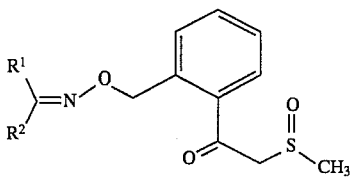

VII

| No. | R⁵ | R⁴ | Data |
|---|---|---|---|
| 1 | —CN | -2-naphthyl | |
| 2 | —CN | -n-hexyl | |
| 3 | —CN | -cyclohexyl | |
| 4 | —CN | -thiophenyl | |
| 5 | —CN | -phenyl | |
| 6 | —CN | -4-Me-phenyl | |
| 7 | —CN | -4-chlorophenyl | |
| 8 | —CN | -4-tert-butyl | |
| 9 | —CN | -2-MeO-phenyl | |
| 10 | —CN | -4-i-Pr—O-phenyl | |
| 11 | —CN | -2-MeS-phenyl | |
| 12 | —CN | -2-fluorophenyl | |
| 13 | —CN | -3-trifluoromethylphenyl | |
| 14 | —CN | -3,5-dichlorophenyl | |
| 15 | —CN | -3-phenylphenyl | |
| 16 | —CN | -4-phenoxyphenyl | |
| 17 | —CN | -3-CH₃(C=N—OMe)-phenyl | |
| 18 | —CN | -3-CH₃(C=N—On—Bu)-phenyl | |
| 19 | —CN | -3-pyridyl | |
| 20 | —CN | -5-pyrimidinyl | |
| 21 | —CN | -3-thienyl | |
| 22 | —CN | -3-indolyl | |
| 23 | —CN | -5-(4-methylthiazolyl) | |
| 24 | —CN | -5-indazolyl | |
| 25 | —CN | -3-(6-chloropyridyl) | |
| 26 | —CH₃ | -2-naphthyl | |
| 27 | —CH₃ | -n-hexyl | |
| 28 | —CH₃ | -cyclohexyl | |
| 29 | —CH₃ | -thiophenyl | |
| 30 | —CH₃ | -phenyl | |
| 31 | —CH₃ | -4-Me-phenyl | IR: 1672; 1038; 969; 930; 755 cm⁻¹ |
| 32 | —CH₃ | -4-chlorophenyl | |
| 33 | —CH₃ | -4-tert-butyl | |
| 34 | —CH₃ | -2-MeO-phenyl | |
| 35 | —CH₃ | -4-i-Pr—O-phenyl | |
| 36 | —CH₃ | -2-MeS-phenyl | |
| 37 | —CH₃ | -2-fluorophenyl | |
| 38 | —CH₃ | -3-trifluoromethylphenyl | |
| 39 | —CH₃ | -3,5-dichlorophenyl | |
| 40 | —CH₃ | -3-phenylphenyl | |
| 41 | —CH₃ | -4-phenoxyphenyl | |
| 42 | —CH₃ | -3-CH₃(C=N—OMe)-phenyl | |
| 43 | —CH₃ | -3-CH₃(C=N—On—Bu)-phenyl | |
| 44 | —CH₃ | -3-pyridyl | |
| 45 | —CH₃ | -5-pyrimidinyl | |
| 46 | —CH₃ | -3-thienyl | |
| 47 | —CH₃ | -3-indolyl | |
| 48 | —CH₃ | -5-(4-methylthiazolyl) | |
| 49 | —CH₃ | -5-indazolyl | |
| 50 | —CH₃ | -3-(6-chloropyridyl) | |
| 51 | —OCH₃ | -2-naphthyl | |
| 52 | —OCH₃ | -n-hexyl | |
| 53 | —OCH₃ | -cyclohexyl | |
| 54 | —OCH₃ | -thiophenyl | |
| 55 | —OCH₃ | -phenyl | |
| 56 | —OCH₃ | -4-Me-phenyl | |
| 57 | —OCH₃ | -4-chlorophenyl | |
| 58 | —OCH₃ | -4-tert-butyl | |
| 59 | —OCH₃ | -2-MeO-phenyl | |
| 60 | —OCH₃ | -4-i-Pr—O-phenyl | |
| 61 | —OCH₃ | -2-MeS-phenyl | |
| 62 | —OCH₃ | -2-fluorophenyl | |
| 63 | —OCH₃ | -3-trifluoromethylphenyl | |
| 64 | —OCH₃ | -3,5-dichlorophenyl | |
| 65 | —OCH₃ | -3-phenylphenyl | |
| 66 | —OCH₃ | -4-phenoxyphenyl | |
| 67 | —OCH₃ | -3-CH₃(C=N—OMe)-phenyl | |

TABLE 6-continued

VII $$\text{structure with } R^1, R^2, \text{N—O—CH}_2\text{-phenyl-C(O)CH}_2\text{-S(O)CH}_3$$

| No. | R⁵ | R⁴ | Data |
|---|---|---|---|
| 68 | —OCH₃ | -3-CH₃(C=N—On—Bu)-phenyl | |
| 69 | —OCH₃ | -3-pyridyl | |
| 70 | —OCH₃ | -5-pyrimidinyl | |
| 71 | —OCH₃ | -3-thienyl | |
| 72 | —OCH₃ | -3-indolyl | |
| 73 | —OCH₃ | -5-(4-methylthiazolyl) | |
| 74 | —OCH₃ | -5-indazolyl | |
| 75 | —OCH₃ | -3-(6-chloropyridyl) | |
| 76 | —NHCH₃ | -2-naphthyl | |
| 77 | —NHCH₃ | -n-hexyl | |
| 78 | —NHCH₃ | -cyclohexyl | |
| 79 | —NHCH₃ | -thiophenyl | |
| 80 | —NHCH₃ | -phenyl | |
| 81 | —NHCH₃ | -4-Me-phenyl | |
| 82 | —NHCH₃ | -4-chlorophenyl | |
| 83 | —NHCH₃ | -4-tert-butyl | |
| 84 | —NHCH₃ | -2-MeO-phenyl | |
| 85 | —NHCH₃ | -4-i-Pr-o-phenyl | |
| 86 | —NHCH₃ | -2-MeS-phenyl | |
| 87 | —NHCH₃ | -2-fluorophenyl | |
| 88 | —NHCH₃ | -3-trifluoromethylphenyl | |
| 89 | —NHCH₃ | -3,5-dichlorophenyl | |
| 90 | —NHCH₃ | -3-phenylphenyl | |
| 91 | —NHCH₃ | -4-phenoxyphenyl | |
| 92 | —NHCH₃ | -3-CH₃(C=N—OMe)-phenyl | |
| 93 | —NHCH₃ | -3-CH₃(C=N—On—Bu)-phenyl | |
| 94 | —NHCH₃ | -3-pyridyl | |
| 95 | —NHCH₃ | -5-pyrimidinyl | |
| 96 | —NHCH₃ | -3-thienyl | |
| 97 | —NHCH₃ | -3-indolyl | |
| 98 | —NHCH₃ | -5-(4-methylthiazolyl) | |
| 99 | —NHCH₃ | -5-indazolyl | |
| 100 | —NHCH₃ | -3-(6-chloropyridyl) | |
| 101 | —SCH₃ | -2-naphthyl | |
| 102 | —SCH₃ | -n-hexyl | |
| 103 | —SCH₃ | -cyclohexyl | |
| 104 | —SCH₃ | -thiophenyl | |
| 105 | —SCH₃ | -phenyl | |
| 106 | —SCH₃ | -4-Me-phenyl | |
| 107 | —SCH₃ | -4-chlorophenyl | |
| 108 | —SCH₃ | -4-tert-butyl | |
| 109 | —SCH₃ | -2-MeO-phenyl | |
| 110 | —SCH₃ | -4-i-Pr—O-phenyl | |
| 111 | —SCH₃ | -2-MeS-phenyl | |
| 112 | —SCH₃ | -2-fluorophenyl | |
| 113 | —SCH₃ | -3-trifluoromethylphenyl | |
| 114 | —SCH₃ | -3,5-dichlorophenyl | |
| 115 | —SCH₃ | -3-phenylphenyl | |
| 116 | —SCH₃ | -4-phenoxyphenyl | |
| 117 | —SCH₃ | -3-CH₃(C=N—OMe)-phenyl | |
| 118 | —SCH₃ | -3-CH₃(C=N—On—Bu)-phenyl | |
| 119 | —SCH₃ | -3-pyridyl | |
| 120 | —SCH₃ | -5-pyrimidinyl | |
| 121 | —SCH₃ | -3-thienyl | |
| 122 | —SCH₃ | -3-indolyl | |
| 123 | —SCH₃ | -5-(4-methylthiazolyl) | |
| 124 | —SCH₃ | -5-indazolyl | |
| 125 | —SCH₃ | -3-(6-chloropyridyl) | |
| 126 | —Me | -2-chlorophenyl | |
| 127 | —Me | -2-Me-phenyl | |
| 128 | —Me | -3-chlorophenyl | |
| 129 | —Me | -3-bromophenyl | |
| 130 | —Me | -4-nitrophenyl | |
| 131 | —Me | -tert-butyl | |
| 132 | —Et | -phenyl | |
| 133 | —Et | -4-chlorophenyl | |
| 134 | —Et | -3,5-dichlorophenyl | |
| 135 | —Et | -2-naphthyl | |

TABLE 6-continued

VII

[Structure: R¹R²C=N-O-CH₂-(phenyl)-C(=O)-CH₂-S(=O)-CH₃]

| No. | R⁵ | R⁴ | Data |
|---|---|---|---|
| 136 | -cyclopropyl | -phenyl | |
| 137 | -cyclopropyl | -4-chlorophenyl | |
| 138 | -cyclopropyl | -3,5-dichlorophenyl | |
| 139 | -cyclopropyl | -4-CH₃O-phenyl | |
| 140 | -cyclopropyl | -4-tBu-phenyl | |
| 141 | -cyclopropyl | -2-naphthyl | |
| 142 | —CN | -2-chlorophenyl | |
| 143 | —CN | -2-Me-phenyl | |
| 144 | —CN | -4-C(H)=N—O—nBu | |

145 [Structure: phthalimide N-O-]

We claim:

1. An o-iminooxymethyl benzoic acid of the formula I

[Structure of formula I: benzene ring with $X_m$ substituent, R¹R²C=N-O-CH₂- group ortho to -C(=O)OH]

wherein m is an integer from 0 to 3,

X is unbranched or branched $C_1$–$C_4$ alkyl; unbranched or branched $C_1$–$C_4$ alkoxy, nitro, cyano or halogen, R¹ is hydrogen; cyano; $C_1$–$C_6$-alkyl; $C_3$–$C_6$-cycloalkyl; $C_1$–$C_4$-alkylthio; $C_1$–$C_4$-alkylthioalkyl; arylthioalkyl; $C_1$–$C_4$-alkoxy; $C_1$–$C_4$-alkoxyalkyl; aryloxyalkyl; $C_1$–$C_4$alkylamino; $C_1$–$C_3$-dialkylamino; benzylamino; benzylthio; benzyloxy; benzyl; vinyl; E-chlorovinyl; E-bromovinyl; $NH_2$; —CO-NHCH₃; —CONHEt; —CONHnPr; —CONHiPr; —CON(CH₃)₂; —CON(Et)₂; —COOCH₃; —COOEt; —COOnPr; or —COOiPr;

R² is $C_1$–$C_4$-alkyl;

phenyl which may be unsubstituted or substituted by 0 to 3 groups selected from $C_1$–$C_4$-alkoxy; $C_1$–$C_4$-alkylthio; fluorine; chlorine; bromine; iodine; $C_1$–$C_4$-alkyl; $C_1$–$C_6$-cycloalkyl; nitro; cyano; trifluoromethyl; trichloromethyl; phenyl; phenoxy; benzyl; benzyloxy; $C_1$–$C_4$-alkylcarbonyl; $C_1$–$C_4$-alkoxycarbonyl; $C_1$–$C_4$-alkylaminocarbonyl; $C_1$–$C_4$-dialkylaminocarbonyl; or $C_1$–$C_4$-dialkylamino; Ph(Me)N—; Ph(Et)N—; Ph(Et)N—; —SO₂Me; —SO₂Et; —SOMe; —SOEt; —SO₂N(Me)₂; —SO₂N(Et)₂; —C(Me)=N—OMe; —C(Me)=N—OEt; —C(Me)=N—OnPr; —C(Me)=N—OiPr; —C(Me)=N—OnBu; —C(Me)=N—OterBu; —C(Me)=N—Obenzyl; —C(Et)=N—OMe; —C(Et)=N—OEt; —C(Et)=N—OnPr; —C(Et)=N—OiPr; —C(Et)=N—OnBu; —C(Et)=N—OtertBu; —C(Et)=N—Obenzyl; —C(nPr)=N—OMe; —C(nPr)=N—OEt; —C(nPr)=N—OnPr; —C(NPr)=N—OiPr; —C(nPr)=N—OnBu; —C(nPr)=N—OtertBu; —C(nPr)=N—Obenzyl; —C(iPr)=N—OMe; —C(iPr)=N—OEt; —C(iPr)=OnPr; —C(iPr)=N—OiPr; —C(iPr)=N—OnBu; —C(iPr)=N—OtertBu; —C(iPr)=N—Obenzyl;

naphthyl which may be unsubstituted or substituted by 0 to 3 groups selected from $C_1$–$C_4$-alkyl; $C_1$–$C_4$-alkoxy; $C_1$–$C_4$-alkylthio; F, Cl, Br, $NO_2$ or CN;

phenylcarbonyl, where the phenyl ring can be substituted by 0 to 3 substituents selected from: methyl, ethyl, n-propyl, i-propyl, n-butyl, tert-butyl, cyclopropyl, MeO, EtO, nPrO, iPrO, MeS, EtS, F, Cl, Br, I, $NO_2$, cyano or trifluoromethyl or the radical

[Structure: R₁R₂C=N-O-]

can have the following meanings

[Structure: indanone oxime N-O-];

[Structure: indanone oxime isomer N-O-];

-continued

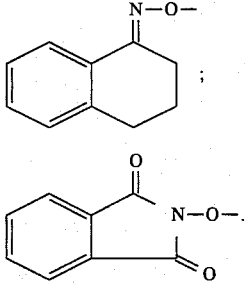

2. The o-iminooxymethyl benzoic acid compound of claim 1, wherein $R^1$ is cyano; $C_1$–$C_6$-alkyl; $C_3$–$C_6$-cycloalkyl; $C_1$–$C_4$-alkoxyalkyl; aryloxyalkyl; benzyl; vinyl; E-chlorovinyl; E-bromovinyl; —CO—NHCH$_3$; —CONHEt; —CONHnPr; —CONHiPr; —CON(CH$_3$)$_2$; —CON(Et)$_2$; —COOCH$_3$; —COOEt; —COOnPr; or —COOiPr;

and wherein $R^2$ is $C_1$–$C_4$-alkyl;

phenyl which may be unsubstituted or substituted by 0 to 3 groups selected from $C_1$–$C_4$-alkoxy; $C_1$–$C_4$-alkylthio; fluorine; chlorine; bromine; iodine; $C_1$–$C_4$-alkyl; $C_1$–$C_6$-cycloalkyl; nitro; cyano; trifluoromethyl; trichloromethyl; phenyl; phenoxy; benzyl; benzyloxy; $C_1$–$C_4$-alkylcarbonyl; $C_1$–$C_4$-alkoxycarbonyl; $C_1$–$C_4$-alkylaminocarbonyl; $C_1$–$C_4$-dialkylaminocarbonyl; or $C_1$–$C_4$-dialkylamino; Ph(Me)N—; Ph(Et)N—; Ph(Et)N—; —SO$_2$Me; —SO$_2$Et; —SOMe; —SOEt; —SO$_2$N(Me)$_2$; —SO$_2$N(Et)$_2$; —C(Me)=N—OMe; —C(Me)=N—OEt; —C(Me)=N—OnPr; —C(Me)=N—OiPr; —C(Me)=N—OnBu; —C(Me)=N—OterBu; —C(Me)=N—Obenzyl; —C(Et)=N—OMe; —C(Et)=N—OEt; —C(Et)=N—OnPr; —C(Et)=N—OiPr; —C(Et)=N—OnBu; —C(Et)=N—OtertBu; —C(Et)=N—Obenzyl; —C(nPr)=N—OMe; —C(nPr)=N—OEt; —C(nPr)=N—OnPr; —C(NPr)=N—OiPr; —C(nPr)=N—OnBu; —C(nPr)=N—OtertBu; —C(nPr)=N—Obenzyl; —C(iPr)=N—OMe; —C(iPr)=N—OEt; —C(iPr)=OnPr; —C(iPr)=N—OiPr; —C(iPr)=N—OnBu; —C(iPr)=N—OtertBu; —C(iPr)=N—Obenzyl;

naphthyl which may be unsubstituted or substituted by 0 to 3 groups selected from $C_1$–$C_4$-alkyl; $C_1$–$C_4$-alkoxy; $C_1$–$C_4$-alkylthio; F, Cl, Br, NO$_2$ or CN; or phenylcarbonyl, where the phenyl ring can be substituted by 0 to 3 substituents selected from: methyl, ethyl, n-propyl, i-propyl, n-butyl, tert-butyl, cyclopropyl, MeO, EtO, nPrO, iPrO, MeS, EtS, F, Cl, Br, I, NO$_2$, cyano or trifluoromethyl.

3. The o-iminooxymethyl benzoic acid of claim 1, wherein m is 0, $R^1$ is CH$_3$ and $R^2$ is 4—Cl—C$_6$H.

* * * * *